(12) United States Patent
Djupesland

(10) Patent No.: US 9,566,402 B2
(45) Date of Patent: Feb. 14, 2017

(54) DELIVERY DEVICE AND METHOD

(71) Applicant: OptiNose AS, Oslo (NO)

(72) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 30 days.

(21) Appl. No.: 14/822,404

(22) Filed: Aug. 10, 2015

(65) Prior Publication Data

US 2016/0184537 A1 Jun. 30, 2016

Related U.S. Application Data

(63) Continuation of application No. 13/724,560, filed on Dec. 21, 2012, now Pat. No. 9,205,209, which is a
(Continued)

(30) Foreign Application Priority Data

May 20, 2003 (GB) .................................. 0311570.6

(51) Int. Cl.
*A61N 1/30* (2006.01)
*A61M 15/00* (2006.01)
(Continued)

(52) U.S. Cl.
CPC ........ *A61M 15/0098* (2014.02); *A61M 15/009* (2013.01); *A61M 15/0021* (2014.02);
(Continued)

(58) Field of Classification Search
CPC ................... A61M 15/0098; A61M 15/0021; A61M 15/009; A61M 15/0091; A61M 15/08; A61M 16/0434; A61M 16/0493; A61M 16/0495; A61M 2016/0021; A61M 2016/0027; A61M 2202/064; A61M 2202/30; A61M 2210/065
(Continued)

(56) References Cited

U.S. PATENT DOCUMENTS 605,436 A  6/1898 Kellogg
642,748 A  2/1900 Manners
(Continued)

FOREIGN PATENT DOCUMENTS

EP  0514085  11/1992
ES  WO 9853869 A1 * 12/1998 ............ A61M 15/08
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Jason Flick
(74) *Attorney, Agent, or Firm* — Finnegan, Henderson, Farabow, Garrett & Dunner, LLP

(57) ABSTRACT

A delivery device for and method of delivering substance, in particular a vaccine, to a mucosal surface within the oral cavity of a subject, the device comprising: a mouthpiece unit to be gripped in the mouth of a subject, wherein the mouthpiece unit is configured such that, on exhalation or attempted exhalation by the subject, a pressure is developed in the oral cavity which is such as to close the oropharyngeal velum of the subject; and an oral outlet unit including at least one outlet from which substance is in use delivered to a mucosal surface within the oral cavity of the subject.

22 Claims, 19 Drawing Sheets

Figure 1:
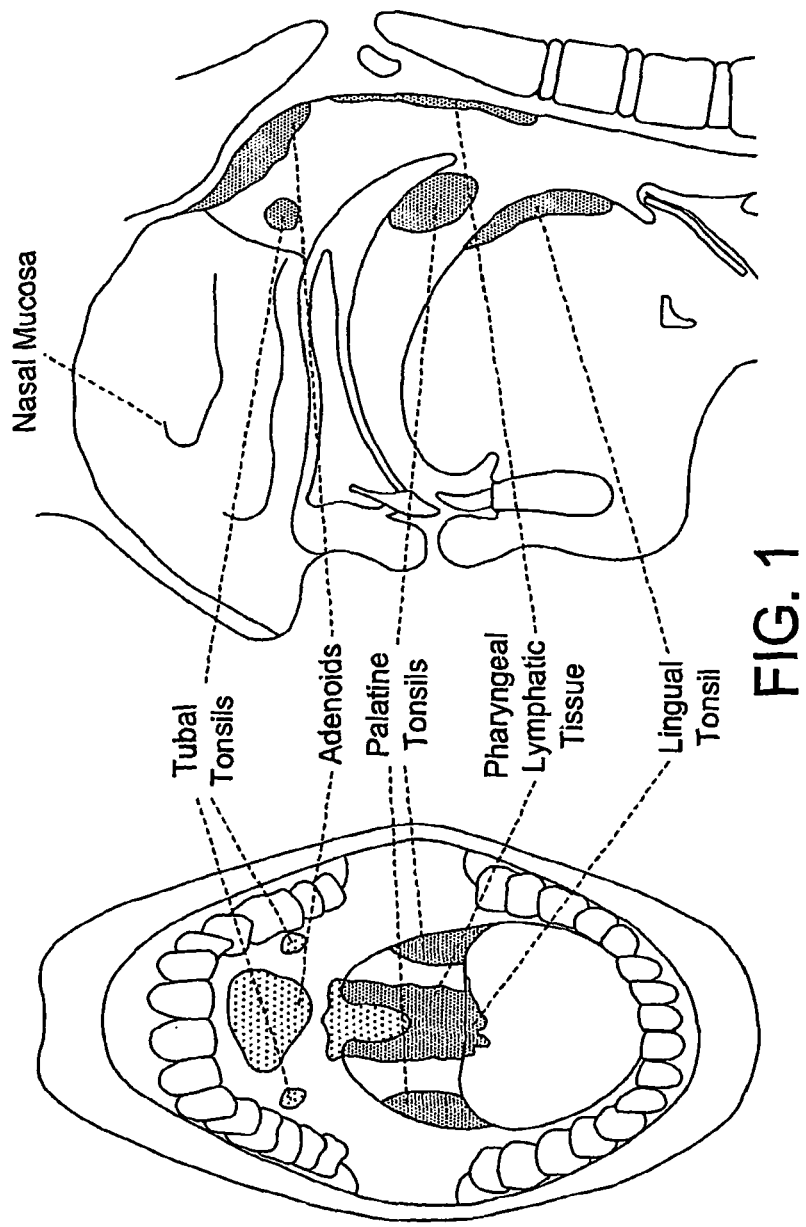

Related U.S. Application Data continuation of application No. 10/557,559, filed as application No. PCT/IB2004/001974 on May 20, 2004, now abandoned.

(51) Int. Cl.
 *A61M 15/08* (2006.01)
 *A61M 16/04* (2006.01)
 *A61M 16/00* (2006.01)

(52) U.S. Cl.
 CPC ........ *A61M 15/0091* (2013.01); *A61M 15/08* (2013.01); *A61M 16/0493* (2014.02); *A61M 16/0495* (2014.02); *A61M 16/0434* (2013.01); *A61M 2016/0021* (2013.01); *A61M 2016/0027* (2013.01); *A61M 2202/064* (2013.01); *A61M 2202/30* (2013.01); *A61M 2210/065* (2013.01)

(58) Field of Classification Search
 USPC .......................................................... 604/19
 See application file for complete search history.

(56) References Cited

U.S. PATENT DOCUMENTS

| | | | |
|---|---|---|---|
| 746,749 | A | 12/1903 | Seidel |
| 5,113,855 | A | 5/1992 | Newhouse |
| 5,443,060 | A | 8/1995 | Visveshwara et al. |
| 5,460,171 | A | 10/1995 | Pesenti et al. |
| 5,622,162 | A | 4/1997 | Johansson et al. |
| 5,672,581 | A | 9/1997 | Rubsamen et al. |
| 5,755,218 | A | 5/1998 | Johansson et al. |
| 5,797,392 | A | 8/1998 | Keldmann et al. |
| 5,813,401 | A | 9/1998 | Radcliff et al. |
| 6,012,454 | A * | 1/2000 | Hodson ............ A61M 15/0028 128/203.15 |
| 6,648,848 | B1 | 11/2003 | Keldmann et al. |
| 6,715,485 | B1 | 4/2004 | Djupesland |
| D530,815 | S | 10/2006 | Murphy et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 7/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |
| 9,108,015 | B2 | 8/2015 | Djupesland |
| 9,119,932 | B2 | 9/2015 | Djupesland |
| 9,132,249 | B2 | 9/2015 | Djupesland |
| 9,144,652 | B2 | 9/2015 | Djupesland et al. |
| 9,168,341 | B2 | 10/2015 | Djupesland |
| 9,205,208 | B2 | 12/2015 | Djupesland |
| 9,205,209 | B2 | 12/2015 | Djupesland |
| 9,272,104 | B2 | 3/2016 | Djupesland |
| 2004/0024330 | A1 | 2/2004 | Djupesland et al. |
| 2004/0112378 | A1 | 6/2004 | Djupesland |
| 2004/0112379 | A1 | 6/2004 | Djupesland |
| 2004/0112380 | A1 | 6/2004 | Djupesland |
| 2004/0149289 | A1 | 8/2004 | Djupesland |
| 2004/0182388 | A1 | 9/2004 | Djupesland |
| 2005/0028812 | A1 | 2/2005 | Djupesland |
| 2005/0072430 | A1 | 4/2005 | Djupesland |
| 2005/0235992 | A1 | 10/2005 | Djupesland |
| 2006/0096589 | A1 | 5/2006 | Djupesland |
| 2006/0107957 | A1 | 5/2006 | Djupesland |
| 2006/0169278 | A1 | 8/2006 | Djupesland et al. |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2007/0186927 | A1 | 8/2007 | Djupesland et al. |
| 2008/0161771 | A1 | 7/2008 | Djupesland |
| 2008/0163874 | A1 | 7/2008 | Djupesland |
| 2008/0221471 | A1 | 9/2008 | Djupesland et al. |
| 2008/0223363 | A1 | 9/2008 | Djupesland |
| 2008/0289629 | A1 | 11/2008 | Djupesland et al. |
| 2009/0101146 | A1 | 4/2009 | Djupesland |
| 2009/0293873 | A1 | 12/2009 | Djupesland et al. |
| 2009/0304802 | A1 | 12/2009 | Djupesland et al. |
| 2009/0314293 | A1 | 12/2009 | Djupesland |
| 2009/0320832 | A1 | 12/2009 | Djupestand |
| 2010/0035805 | A1 | 2/2010 | Hafner |
| 2010/0051022 | A1 | 3/2010 | Djupesland et al. |
| 2010/0057047 | A1 | 3/2010 | Djupesland et al. |
| 2010/0242959 | A1 | 9/2010 | Djupesland et al. |
| 2010/0282246 | A1 | 11/2010 | Djupesland et al. |
| 2010/0288275 | A1 | 11/2010 | Djupesland et al. |
| 2010/0300439 | A1 | 12/2010 | Djupesland et al. |
| 2011/0023869 | A1 | 2/2011 | Djupesland |
| 2011/0053827 | A1 | 3/2011 | Hafner |
| 2011/0088690 | A1 | 4/2011 | Djupesland et al. |
| 2011/0088691 | A1 | 4/2011 | Djupesland |
| 2011/0114087 | A1 | 5/2011 | Djupesland et al. |
| 2011/0126830 | A1 | 6/2011 | Djupesland et al. |
| 2011/0259329 | A1 | 10/2011 | Djupesland et al. |
| 2011/0318345 | A1 | 12/2011 | Djupesland |
| 2012/0000459 | A1 | 1/2012 | Djupesland |
| 2012/0006323 | A1 | 1/2012 | Djupesland |
| 2012/0073571 | A1 | 3/2012 | Djupesland |
| 2012/0090608 | A1 | 4/2012 | Djupesland et al. |
| 2012/0260915 | A1 | 10/2012 | Djupesland |
| 2013/0098362 | A1 | 4/2013 | Djupesland et al. |
| 2013/0125889 | A1 | 5/2013 | Djupesland et al. |
| 2013/0327320 | A1 | 12/2013 | Djupesland |
| 2014/0018295 | A1 | 1/2014 | Djupesland |
| 2014/0041660 | A1 | 2/2014 | Djupesland et al. |
| 2014/0060536 | A1 | 3/2014 | Djupesland |
| 2014/0073562 | A1 | 3/2014 | Djupesland |
| 2014/0144442 | A1 | 5/2014 | Djupesland et al. |
| 2014/0144443 | A1 | 5/2014 | Djupesland et al. |
| 2014/0166008 | A1 | 6/2014 | Djupesland |
| 2014/0202456 | A1 | 7/2014 | Djupesland |
| 2014/0246022 | A1 | 9/2014 | Djupesland et al. |
| 2015/0007811 | A1 | 1/2015 | Djupesland et al. |
| 2015/0013670 | A1 | 1/2015 | Djupesland et al. |
| 2015/0013677 | A1 | 1/2015 | Djupesland et al. |
| 2015/0053201 | A1 | 2/2015 | Djupesland et al. |
| 2015/0090259 | A1 | 4/2015 | Djupesland et al. |
| 2015/0101605 | A1 | 4/2015 | Djupesland et al. |
| 2015/0144129 | A1 | 5/2015 | Djupesland et al. |
| 2015/0165139 | A1 | 6/2015 | Hafner |
| 2015/0182709 | A1 | 7/2015 | Djupesland |
| 2015/0246194 | A1 | 9/2015 | Djupesland et al. |
| 2015/0367090 | A1 | 12/2015 | Djupesland et al. |
| 2015/0367091 | A1 | 12/2015 | Djupesland et al. |
| 2016/0001022 | A1 | 1/2016 | Djupesland et al. |

(56) References Cited

U.S. PATENT DOCUMENTS

| | | |
|---|---|---|
| 2016/0045687 A1 | 2/2016 | Djupesland |
| 2016/0051778 A1 | 2/2016 | Djupesland et al. |
| 2016/0074603 A1 | 3/2016 | Djupesland et al. |

FOREIGN PATENT DOCUMENTS

| | | |
|---|---|---|
| GB | 2397025 | 7/2004 |
| JP | 026002 | 6/1927 |
| JP | 2001/526577 | 12/2001 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/045482 | 6/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The Target Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

* cited by examiner

DELIVERY DEVICE AND METHOD

This is a continuation application of U.S. application Ser. No. 13/724,560 filed Dec. 21, 2012, now pending, that is a continuation of U.S. application Ser. No. 10/557,559 filed Sep. 13, 2006, now abandoned, that is the national stage entry of PCT/IB2004/001974 filed May 20, 2004, that claims priority to GB 0311570 filed May 20, 2003, the entire contents of each of which are incorporated herein by reference.

The present invention relates to a delivery device and method for the delivery of substance, in particular vaccines, but also medicaments, to mucosal surfaces, and in particular lymphoid structures in the oral cavity.

Currently almost all vaccines are administered by injection. Whilst injection is effective, the use of needles leads both to contamination and transmission of infectious diseases, the treatment of which incurs very significant costs. This problem arises particularly in developing countries. Also, the current vaccine formulations require the use of expensive cold-chains.

It is thus an aim of the present invention to provide a delivery technique which provides for the needleless delivery of vaccines, and indeed medicaments.

Vaccination constitutes one of the most cost-effective preventative measures against illness and death from infection. More than 90% of all infections use the mucosa as portals of entry. There is thus great interest in exploiting mucosal immunity, particularly by inducing the local production of secretory immunoglobulin A (SIgA) antibodies which may block epithelial colonization and penetration of pathogens into the body. However, complete protection against many infectious agents would, in addition, require the induction of systemic humoral immunity (particularly IgG antibodies) and cytotoxic T lymphocytes (CTLs). Interestingly, vaccines which are delivered through mucosal surfaces to elicit secretory immunity, often also induce systemic immunity, depending on the route and the concurrently applied adjuvant.

A particular advantage of mucosal vaccines is that those vaccines can be delivered other than by way of injection through needles, thereby providing for an immunization regime which is much safer and more suited to mass use, and being particularly attractive to mass vaccination in developing countries.

It is a particular aim of the present invention to provide a delivery device and method which provides for vaccination through mucosal surfaces of the nasopharynx in enhancing the mucosal immune response by targeting the large population of dendritic, antigen-presenting cells (APCs) of the nasal mucosa and the lymphatic structures of Waldeyer's ring. FIG. 1 illustrates the upper respiratory tract of a human subject, and in particular the lymphoid structures of Waldeyer's ring.

The present inventor believes that there is good reason to assume that the paired palatine tonsils and the unpaired nasopharyngeal tonsils, the adenoids, are equivalents of the paired nasopharynx-associated lymphoid tissue (NALT) structures of rodents, where the tonsils have structures which provide for superior antigen-trapping because of the deep and branched crypts. These crypts are covered by a reticulated epithelium which is adapted for the uptake of antigens, and in addition contain antigen-transporting M cells.

Although nasal mucosal vaccination has several advantages over oral vaccination, which is achieved primarily through intestinal delivery which targets the gut-associated lymphoid tissue (GALT), there are a number of current issues regarding nasal mucosal vaccination, as will be mentioned in more detail hereinbelow.

The inductive sites in the GALT, such as Peyer's patches, do not possess antigen-retaining crypts. Animal experiments have suggested that the dose of a dead antigen has to be increased several times to obtain an acceptable immune response in the GALT as compared to that obtained by administration through the nasal mucosa. This low immune response in GALT administration arises because the structure of the GALT is designed primarily for the uptake of proliferating or M cell-binding agents, whereas soluble antigens are most likely taken up through the extensive surface epithelium in the gut. Furthermore, while within the gut lumen, soluble antigens are attacked by proteolytic enzymes, leading to extensive degradation, which is not the case in the upper airway. In murine vaccine models, this effect is exacerbated by the fact that some 50% of the IgA-producing cells in the lamina propria are derived from the peritoneal cavity (B1 cells) and produce low-affinity antibodies against the commensal microbiota.

Nasal mucosal administration also appears to elicit improved systemic immunity as compared to oral administration, and mucosal tolerance induction, which may compromise local vaccination, is not so easily induced in the mucosa of the airways as in the gut.

There are other alternative mucosal sites for vaccine administration, but these are likely to be less socially acceptable, for example, rectal and vaginal routes. Moreover, inductive mucosal-associated lymphoid tissues (MALT) are not present in the genital tract, and it is not easy to control how such organized lymphoid tissue of the large bowel, the isolated lymphoid follicles (ILFs), would be targeted by a rectally-applied vaccine.

Moreover, reduced immune response with aging occurs faster in the GALT than in the NALT, which is particularly relevant when considering the vaccination of older subjects, typically geriatric subjects.

Currently, a critical issue in nasal vaccine administration is the potential access to the central nervous system through the olfactory region. The current thinking is that it is desirable to work with dead vaccines and non-neurotoxic adjuvants for nasal vaccine administration.

An alternative to nasal administration is targeted delivery to lymphatic structures in the oral cavity, which include the palatine tonsils, the lingual tonsil and the lymphatic aggregates on the posterior pharyngeal wall. Preliminary studies have indicated the feasibility of such administration, in providing a satisfactory immune response, where targeted delivery can be achieved.

In one aspect the present invention provides a delivery device for delivering substance to a mucosal surface within the oral cavity of a subject, the device comprising: a mouthpiece unit to be gripped in the mouth of a subject, wherein the mouthpiece unit is configured such that, on exhalation or attempted exhalation by the subject, a pressure is developed in the oral cavity which is such as to close the oropharyngeal velum of the subject; and an oral outlet unit including at least one substance outlet from which substance is in use delivered to a mucosal surface within the oral cavity of the subject.

In another aspect the present invention provides a delivery device for delivering substance to a mucosal surface within the oral cavity of a subject, the device comprising: a mouthpiece unit for fitting to the mouth of a subject; and an oral outlet unit including at least one substance outlet from which substance is in use delivered to a mucosal surface within the oral cavity of the subject.

In a further aspect the present invention provides a method of delivering substance to a mucosal surface within the oral cavity of a subject, the method comprising the steps of: a subject exhaling or attempting to exhale into a mouthpiece unit to develop a pressure in the oral cavity which is such as to close the oropharyngeal velum of the subject; and delivering substance to a mucosal surface within the oral cavity of the subject.

In a yet further aspect the present invention provides a method of delivering substance to a mucosal surface within the oral cavity of a subject, the method comprising the steps of: providing a delivery device comprising a mouthpiece unit for fitting to the mouth of a subject, and an oral outlet unit including at least one substance outlet from which substance is deliverable; fitting the mouthpiece unit in the mouth of the subject; and delivering substance to a mucosal surface within the oral cavity of the subject.

In providing for delivery to structures in the oral cavity, where the oropharyngeal velum is closed during delivery so as to prevent communication with the nasal cavity, delivery of live attenuated vaccines and drugs incorporating adjuvants based on neurotoxins, such as Cholera toxin derivatives and *E-coli* derivatives, can be achieved.

Figure 3A:
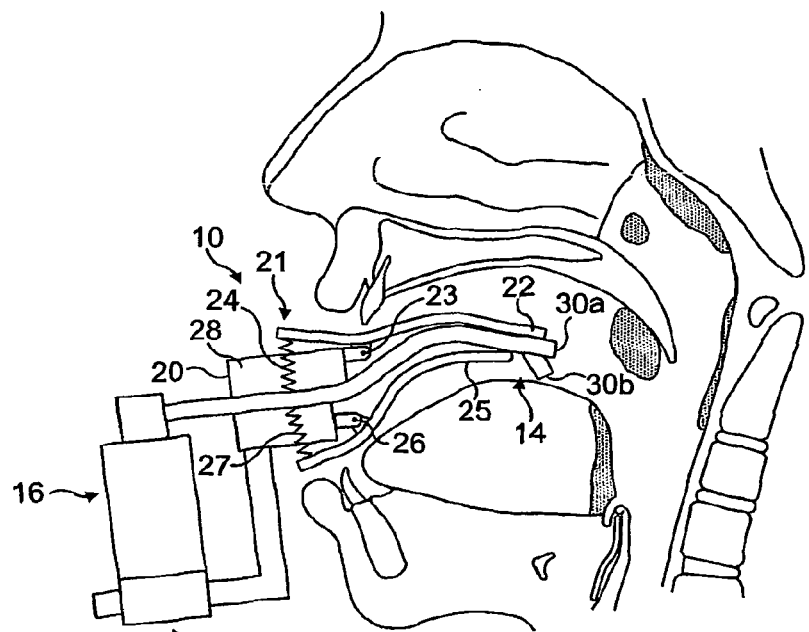
Figure 3B:
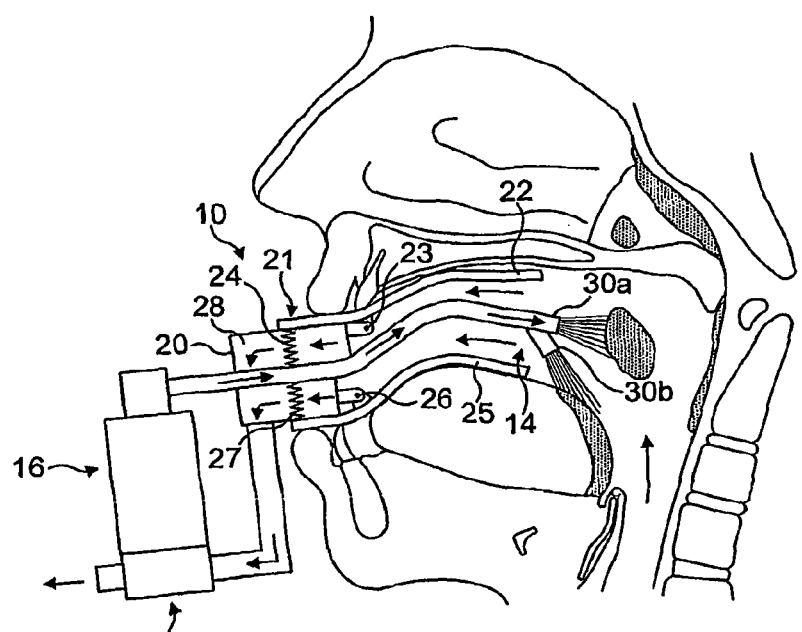
Figure 4A:
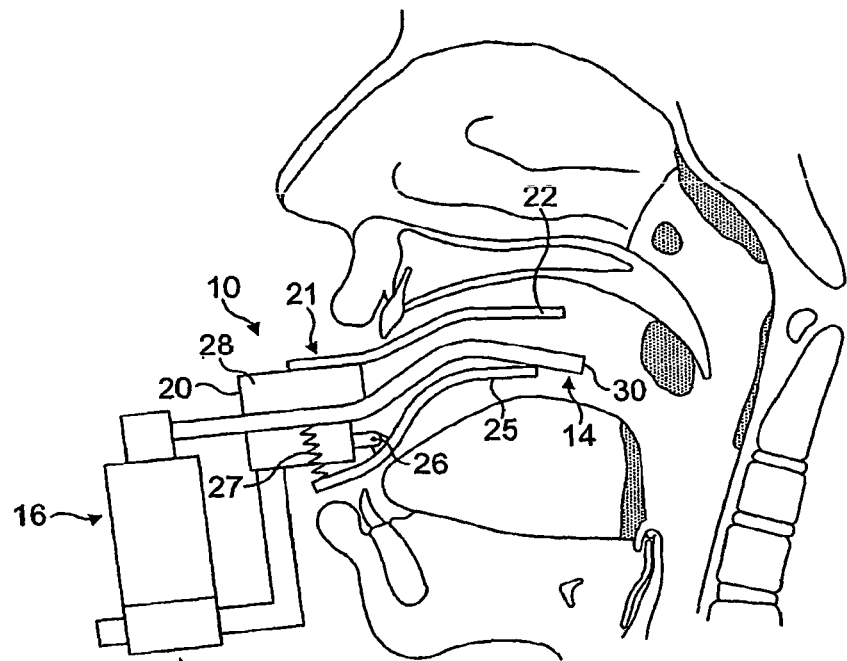
Figure 4B:
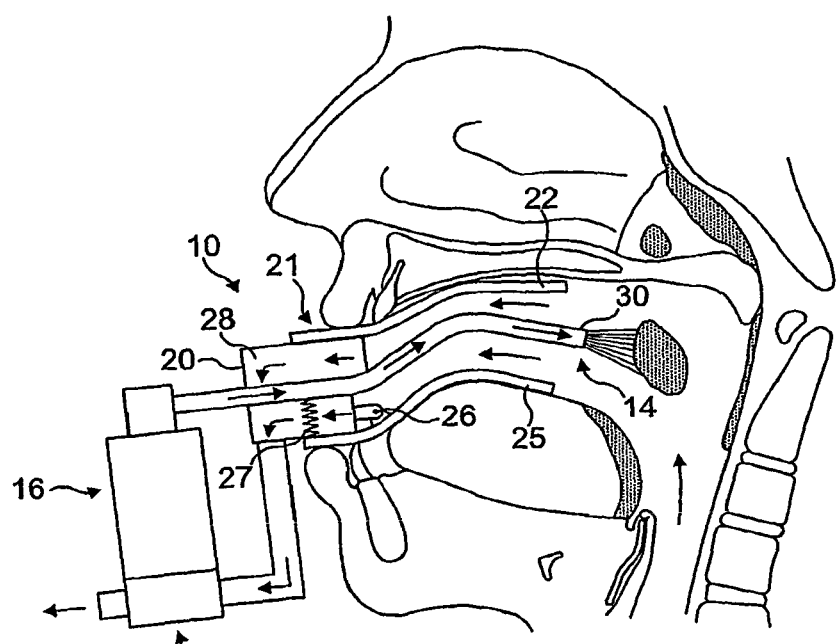
Figure 5A:
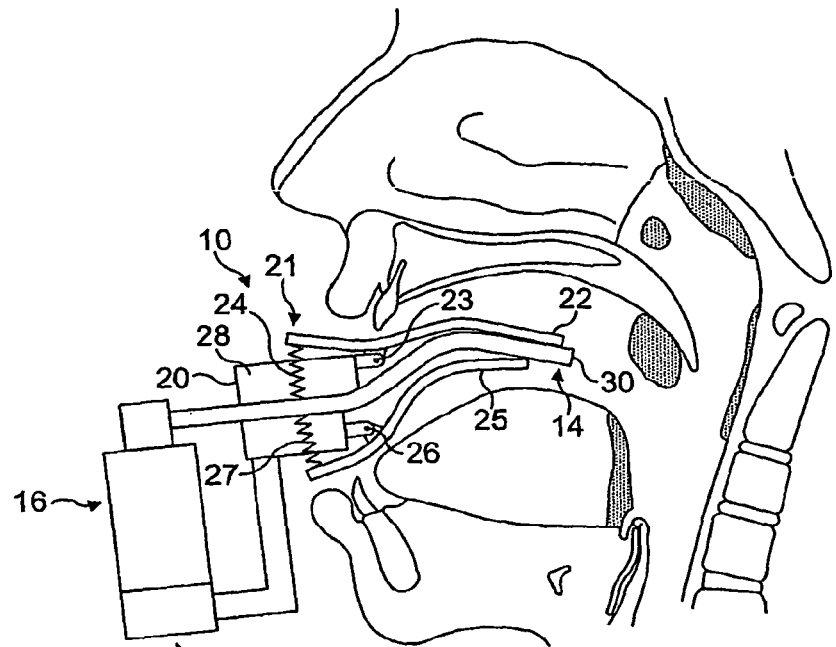
Figure 5B:
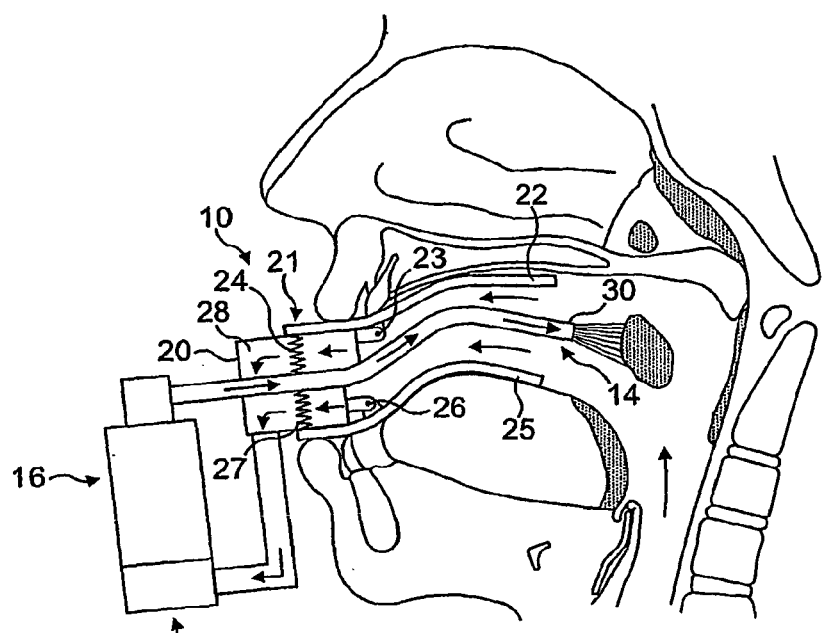
Figure 6A:
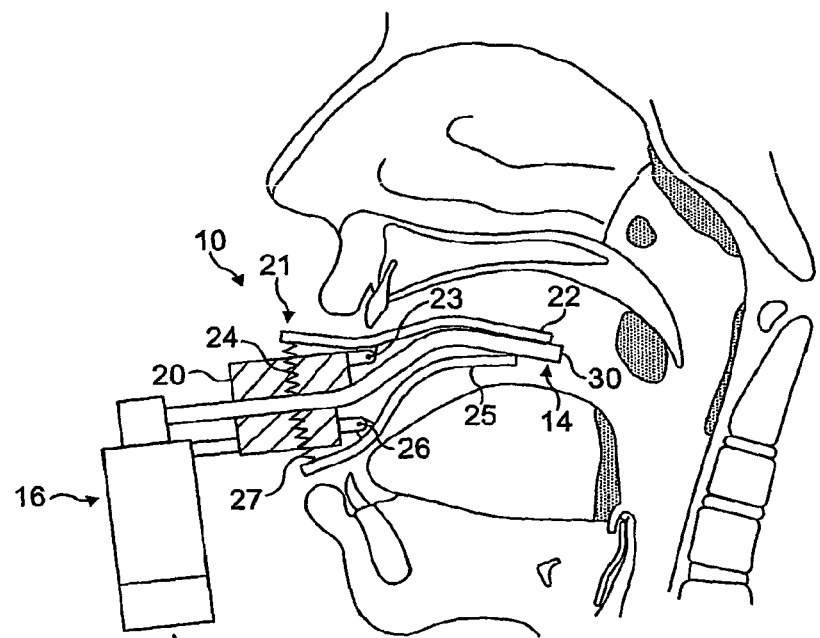
Figure 6B:
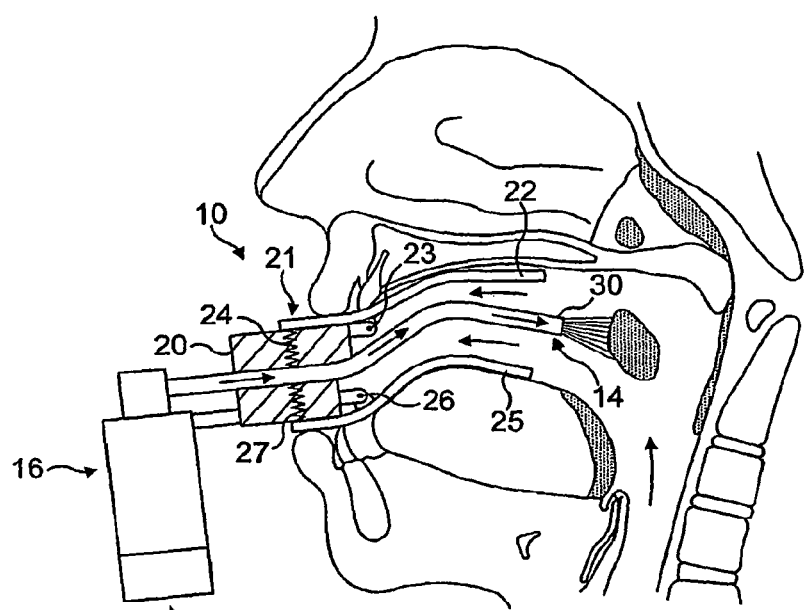
Figure 10A:
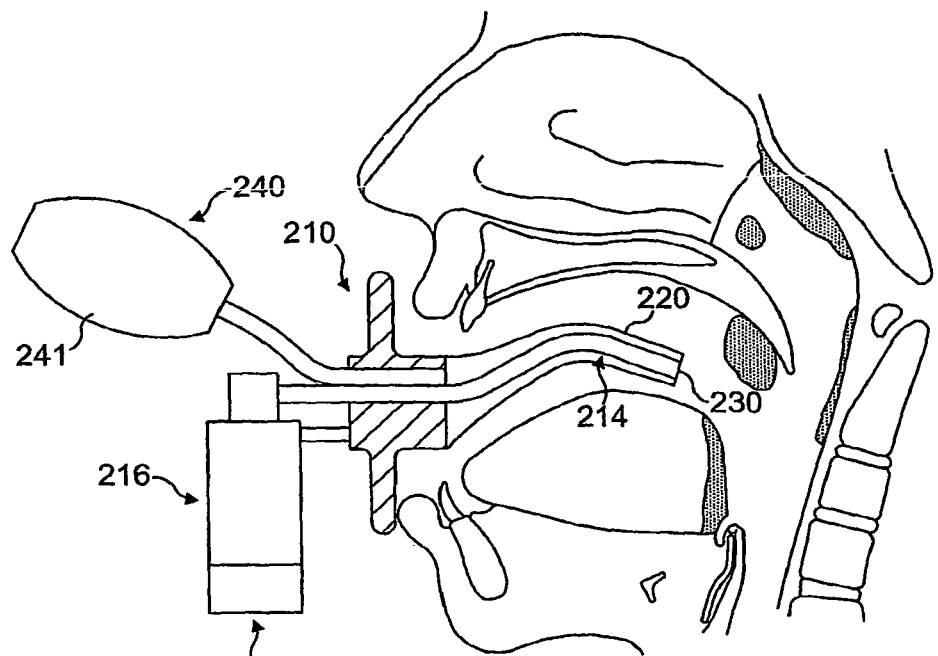
Figure 10B:
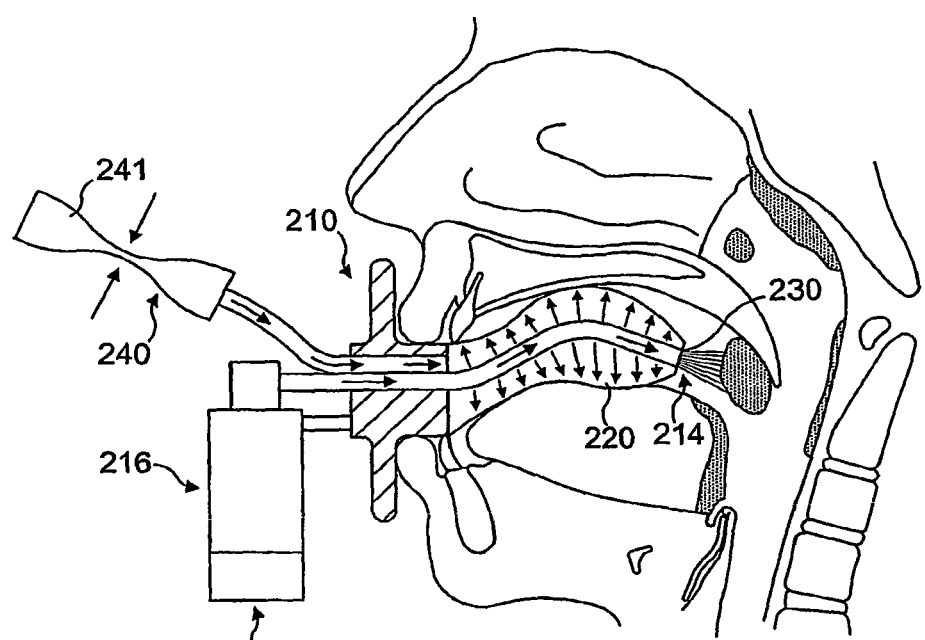
Figure 13A:
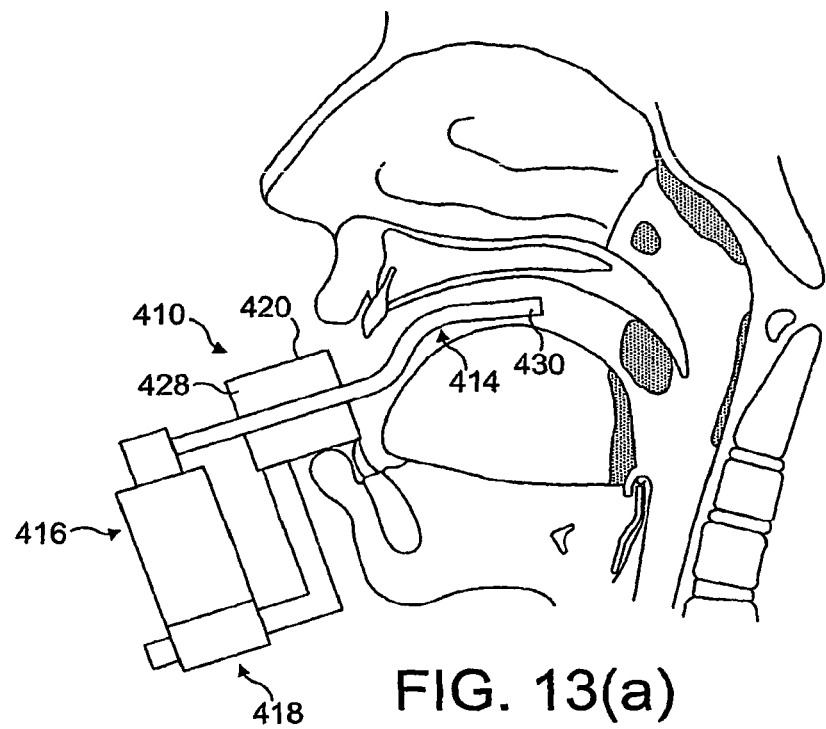
Figure 13B:
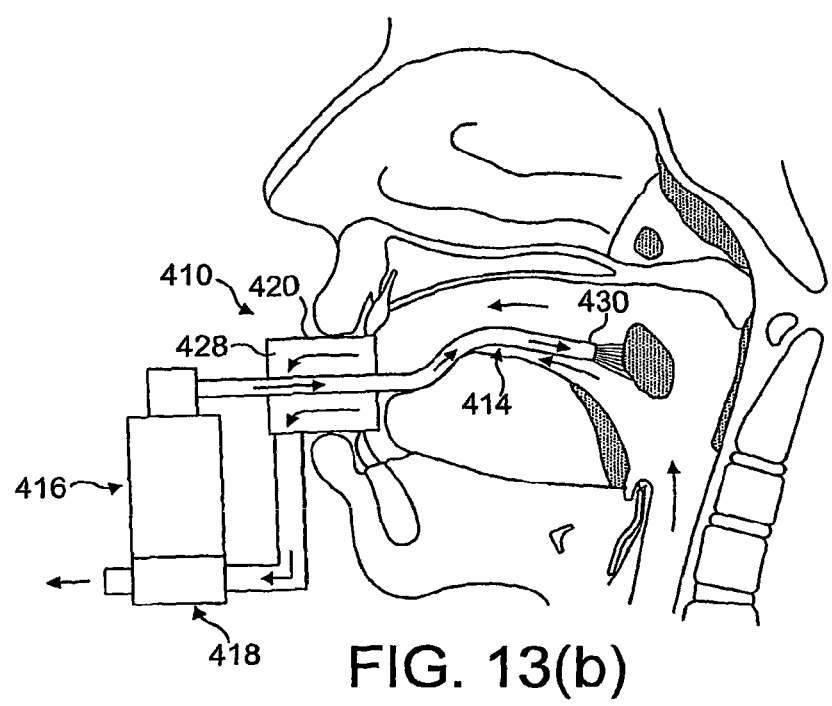
Figure 14A:
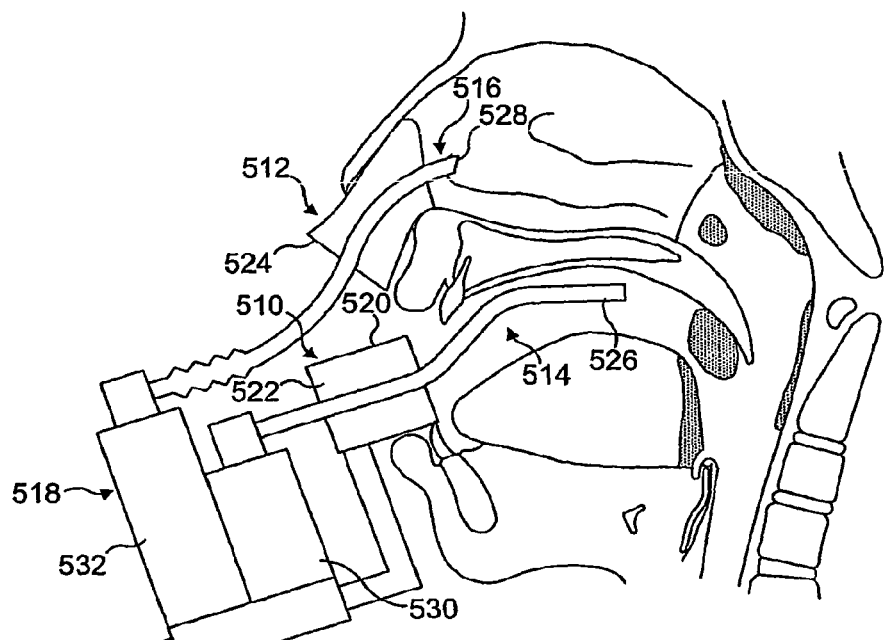
Figure 14B:
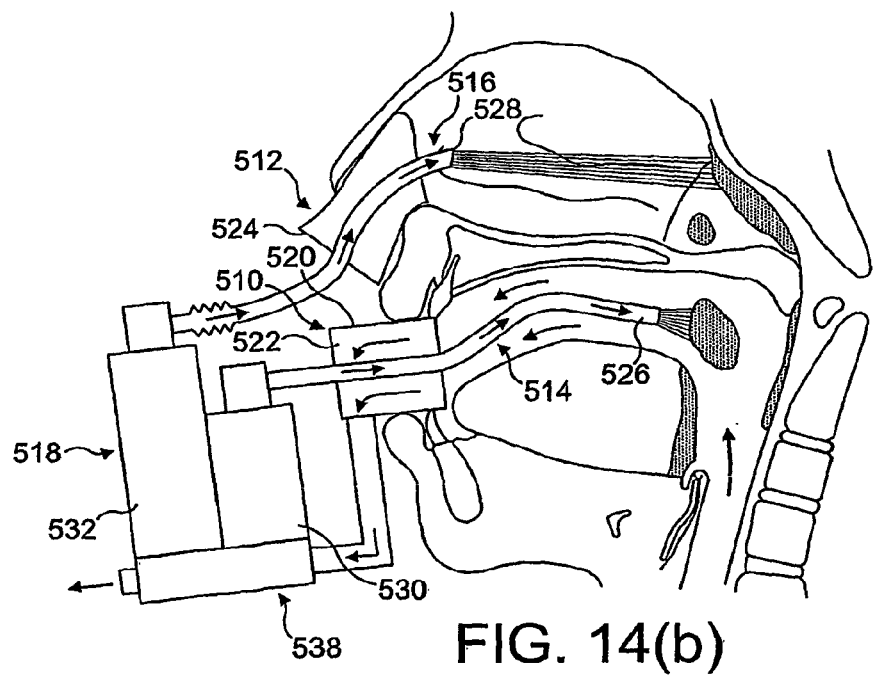
Figure 15A:
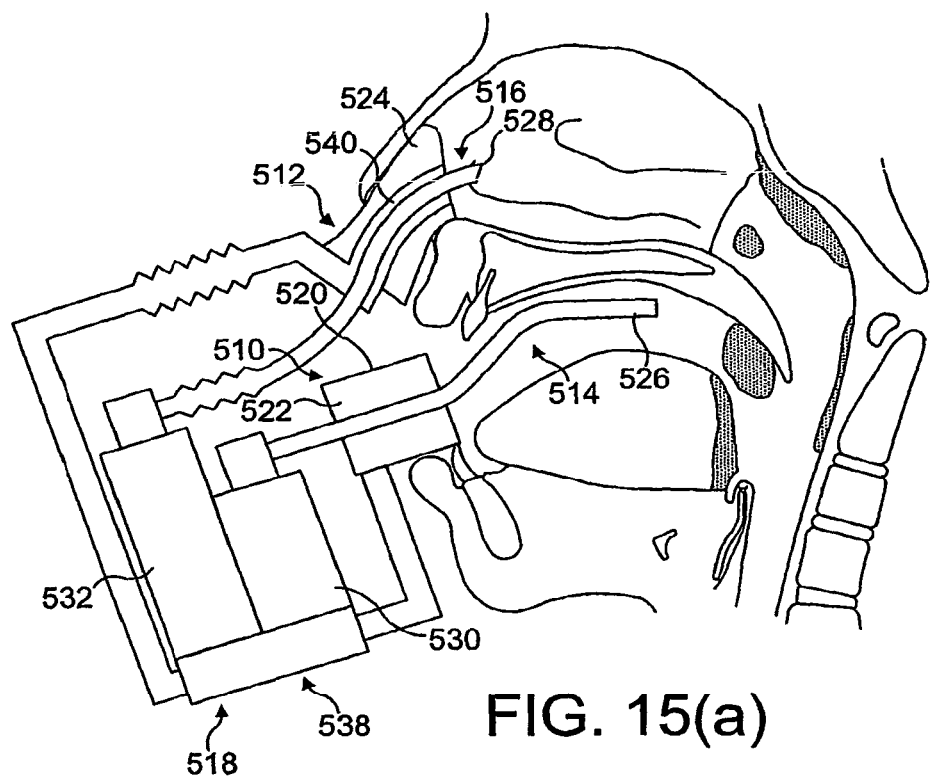
Figure 15B:
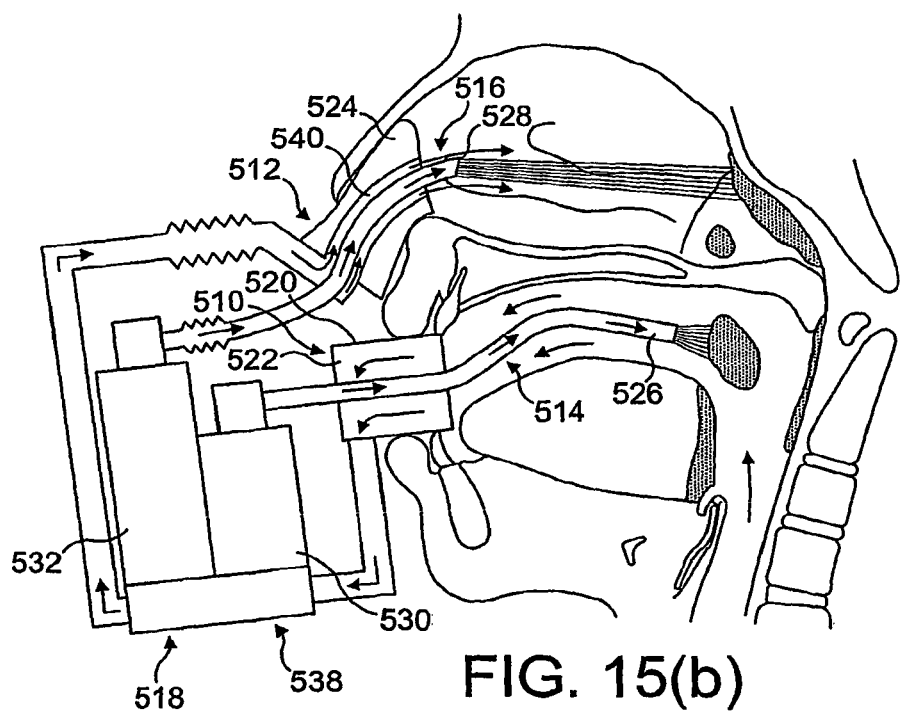
Figure 16A:
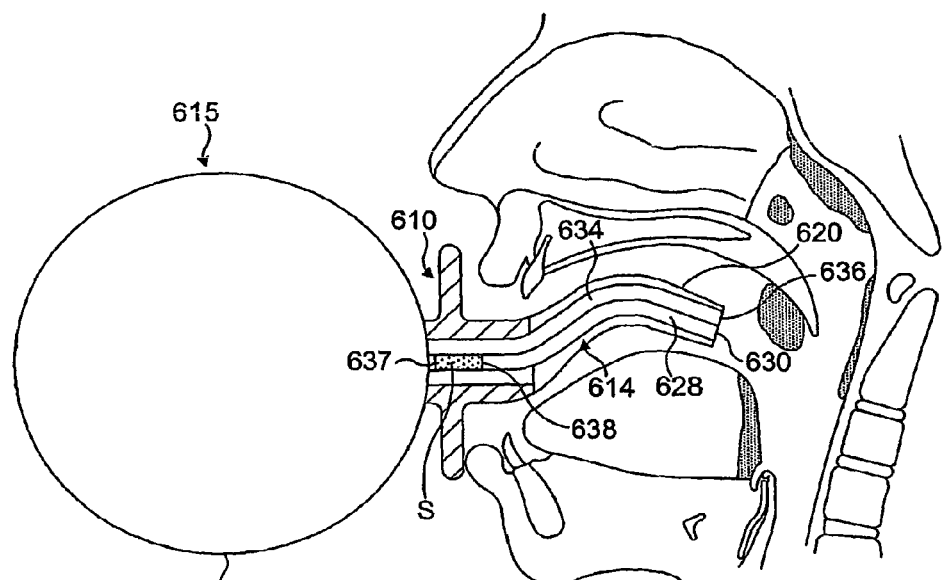
Figure 16B:
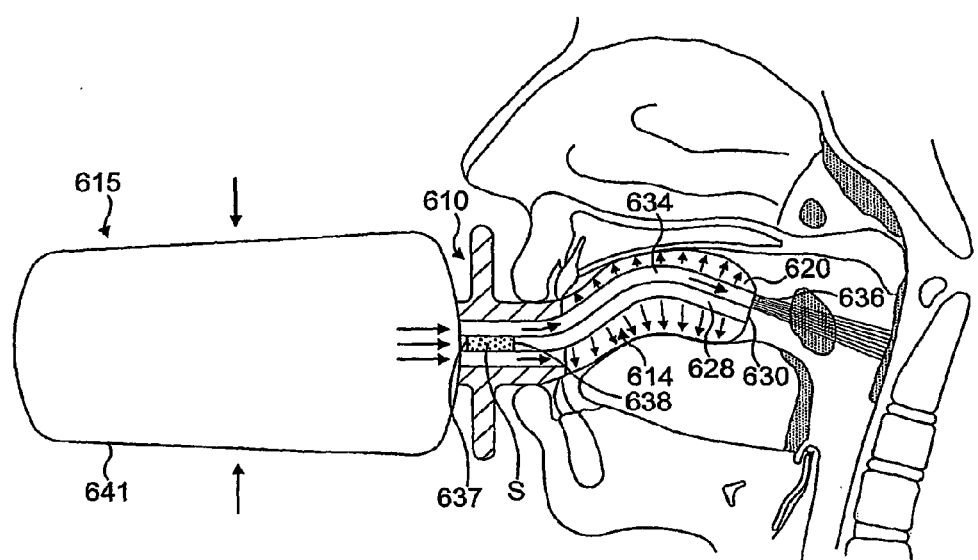
Figure 16C:
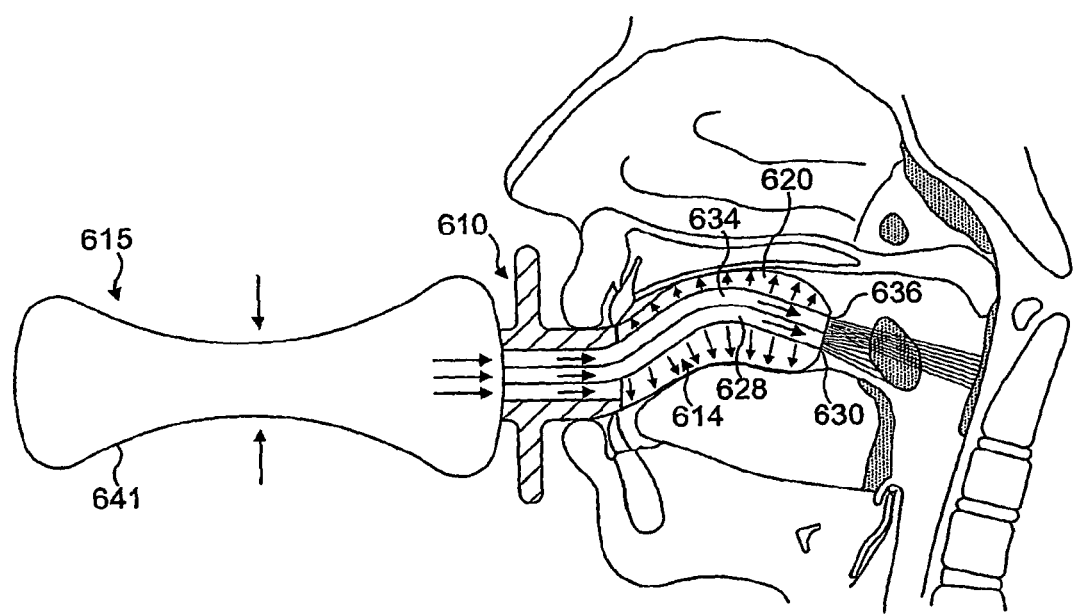

Preferred embodiments of the present invention will now be described hereinbelow by way of example only with reference to the accompanying drawings, in which:

FIG. 1 schematically represents the upper respiratory tract of a human subject;

FIGS. 2(*a*) and (*b*) illustrate a delivery device in accordance with a first embodiment of the present invention;

FIGS. 3(*a*) and (*b*) illustrate a delivery device in accordance with a second embodiment of the present invention;

FIGS. 4(*a*) and (*b*) illustrate a delivery device in accordance with a third embodiment of the present invention;

FIGS. 5(*a*) and (*b*) illustrate a delivery device in accordance with a fourth embodiment of the present invention;

FIGS. 6(*a*) and (*b*) illustrate a delivery device in accordance with a fifth embodiment of the present invention;

FIGS. 7(*a*) and (*b*) illustrate a delivery device in accordance with a sixth embodiment of the present invention;

FIG. 8(*a*) to (*c*) illustrate a delivery device in accordance with a seventh embodiment of the present invention;

FIG. 9(*a*) to (*c*) illustrate a delivery device in accordance with an eighth embodiment of the present invention;

FIGS. 10(*a*) and (*b*) illustrate a delivery device in accordance with a ninth embodiment of the present invention;

FIGS. 11(*a*) and (*b*) illustrate a delivery device in accordance with a tenth embodiment of the present invention;

FIGS. 12(*a*) and (*b*) illustrate a delivery device in accordance with an eleventh embodiment of the present invention;

FIGS. 13(*a*) and (*b*) illustrate a delivery device in accordance with a twelfth embodiment of the present invention;

FIGS. 14(*a*) and (*b*) illustrate a delivery device in accordance with a thirteenth embodiment of the present invention;

FIGS. 15(*a*) and (*b*) illustrate a delivery device in accordance with a fourteenth embodiment of the present invention; and FIG. 16(*a*) to (*c*) illustrate a delivery device in accordance with a fifteenth embodiment of the present invention.

FIGS. 2(*a*) and (*b*) illustrate a breath-actuated delivery device in accordance with a first embodiment of the present invention.

The delivery device comprises a mouthpiece unit 10 which is gripped in the mouth of a user and through which the user exhales to actuate the delivery device, an outlet unit 14 which extends into the oral cavity of the user and through which substance is delivered to mucosal surfaces of the oral cavity, a substance supply unit 16 for delivering metered doses of substance to the outlet unit 14, and a breath-actuated trigger unit 18 for actuating the substance supply unit 16 in response to exhalation by the user.

In this embodiment the substance is a vaccine, but in alternative embodiments can be a medicament.

The mouthpiece unit 10 includes a mouthpiece 20 which is configured to be gripped between the teeth or gums of the user on the user biting thereon, with the lips of the user providing a seal to the mouthpiece 20, and a positioning mechanism 21 which acts both to fix the position of the outlet unit 14 relative to the hard palate and depress the tongue when the user is biting on the mouthpiece 20, thereby directing the outlet unit 14 towards a targeted mucosal surface as will be described in more detail hereinbelow.

The positioning mechanism 21 comprises a first, upper arm 22 which is disposed to an upper part of the mouthpiece 20 and hinged to the mouthpiece 20 about a pivot 23 such as to be movable between a first, closed position, as illustrated in FIG. 2(*a*), and a second, open position, as illustrated in FIG. 2(*b*), and a first biasing element 24 which acts to bias the upper arm 22 to the closed position. In the closed position, which is the position which the upper arm 22 normally adopts under the bias of the first biasing element 24, the inner end of the upper arm 22 is located adjacent the outlet unit 14 such as to allow for easy insertion together with the outlet unit 14 into the mouth of the user. In the open position, which is achieved on the user biting on the mouthpiece 20, where, in the biting action, the teeth or gums act on the outer end of the upper arm 22 against the bias of the first biasing element 24, the upper arm 22 is hinged about the pivot 23 such as to cause the outward movement of the inner end of the upper arm 22. In this open position, the inner end of the upper arm 22 is spaced from the outlet unit 14 by a predetermined distance and provides that the outlet unit 14 is spaced by the predetermined distance from the hard palate, which is a fixed point of reference, when the upper arm 22 engages the same, thereby providing that the outlet unit 14 is directed to a targeted mucosal surface on operation of the positioning mechanism 21.

The positioning mechanism 21 further comprises a second, lower arm 25 which is disposed to a lower part of the mouthpiece 20 and hinged to the mouthpiece 20 about a pivot 26 such as to be movable between a first, closed position, as illustrated in FIG. 2(*a*), and a second, open position, as illustrated in FIG. 2(*b*), and a second biasing element 27 which acts to bias the lower arm 25 to the closed position. In the closed position, which is the position which the lower arm 25 normally adopts under the bias of the second biasing element 27, the inner end of the lower arm 25 is located adjacent the outlet unit 14 such as to allow for easy insertion together with the outlet unit 14 into the mouth of the user. In the open position, which is achieved on the user biting on the mouthpiece 20, where, in the biting action, the teeth or gums act on the outer end of the lower arm 25 against the bias of the second biasing element 27, the lower arm 25 is hinged about the pivot 26 such as to cause the outward movement of the inner end of the lower arm 25. In this open position, the inner end of the lower arm 25 is spaced from the outlet unit 14 and acts to depress the tongue so as to facilitate access to the rear of the oral cavity.

Through the provision of the positioning mechanism 21, the biting action of the user, here on the mouthpiece 20, acts to direct the outlet unit 14 at a targeted mucosal surface by the positional relationship between the outlet unit 14 and the upper arm 22 of the positioning mechanism 21 when in the open position, and causes the depression of the tongue which facilitates access to the rear of the oral cavity, in particular the mucosal surfaces of the lymphoid structures to the rear of the oral cavity. As illustrated in FIG. 1, the tongue ordinarily rests close to the hard palate and thereby obstructs direct access to the mucosal surfaces of the lymphoid structures in the oral cavity, notably the palatine tonsils and the lingual tonsil. Whilst elongate delivery devices have been developed to effect delivery to oral mucosal tissue, such delivery devices require a skilled operator to position the same and rely solely on the mechanical action of the delivery device in moving the tongue to access oral mucosal tissue.

In this embodiment the mouthpiece 20 includes a flow channel 28 through which an air flow generated on exhalation by the user is directed. The flow channel 28 is configured to provide a flow resistance to an exhalation air flow which is such as to generate a positive pressure in the oral cavity. This positive pressure is such as to cause closure of the oropharyngeal velum of the user, thereby isolating the oral cavity from the nasal cavity, and preventing the communication of substance to the nasal cavity where delivered to the oral cavity. The present inventor has also identified that this positive pressure acts to cause depression of the tongue which facilitates access to the mucosal surfaces of the lymphoid structures to the rear of the oral cavity. In one embodiment the mouthpiece 20 can include a collection element, typically a filter, to collect the delivered substance which is entrained by the exhalation breath and delivered therethrough.

In this embodiment the outlet unit 14 includes at least one outlet 30, in this embodiment a single nozzle, for delivering substance at a targeted mucosal surface to the rear of the oral cavity, here of the palatine tonsils. The extent of the outlet unit 14 is configured to position the at least one outlet 30 thereof as far as possible to the rear of the oral cavity without causing discomfort or inducing the vomiting reflexes. In one embodiment the outlet unit 14 can be provided as a flexible unit, with the at least one outlet 30 being fixed to the upper arm 22 of the positioning mechanism 21.

In this embodiment the at least one outlet 30 is configured to provide a focused spray onto the targeted mucosal surface. In an alternative embodiment the at least one outlet 30 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 16 comprises an aerosol canister for delivering metered doses of substance in a volume of propellant, preferably a hydrofluoroalkane (HFA) propellant or the like, which is fluidly connected to the outlet unit 14 to deliver substance from the at least one outlet 30 thereof.

In this embodiment the substance supply unit 16 is a multi-dose unit for delivering a plurality of metered doses of substance. In another embodiment the substance supply unit 16 could be a single-dose unit for delivering a single metered dose of substance. In this embodiment the substance supply unit 16 and the trigger unit 18 could be configured such as in use to be located within the oral cavity, with the mouthpiece unit 10 including a shield, much in the manner of a dummy or soother for an infant, to prevent any possibility of the device being swallowed. This embodiment lends itself to fabrication from inexpensive plastics, and in particular biodegradable materials.

The substance supply unit 16 is pre-primeable, in this embodiment by loading a resilient element, and is coupled to the trigger unit 18 such that, when the trigger unit 18 is actuated by the exhalation breath of the user, the resilient element is released to actuate the substance supply unit 16 to deliver a metered dose of substance through the at least one outlet 30 as a focused spray.

In this embodiment the trigger unit 18 is configured to cause actuation of the substance supply unit 16 on generation of a predetermined pressure thereat.

In an alternative embodiment the trigger unit 18 could be configured to cause actuation of the substance supply unit 16 on generation of a predetermined air flow therethrough.

In an alternative embodiment the substance supply unit 16 could comprise a mechanical delivery pump, in particular a liquid delivery pump or a powder delivery pump, which delivers metered doses of substance on actuation thereof.

In another alternative embodiment the substance supply unit 16 could comprise a dry powder delivery unit which delivers metered doses of substance on actuation thereof.

Operation of the delivery device will now be described hereinbelow.

Figure 2A:
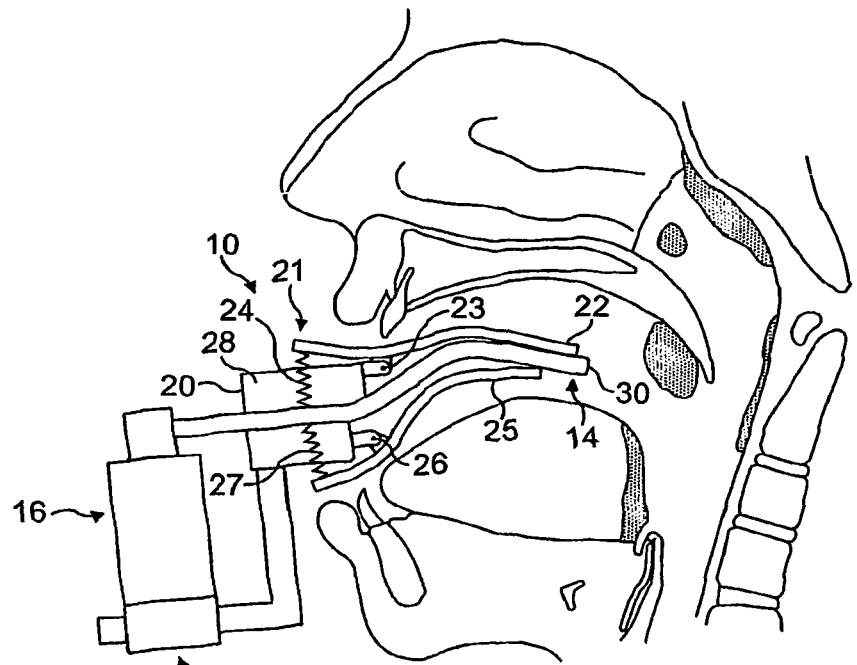

Referring to FIG. 2(a), the outlet unit 14 is first inserted into the oral cavity of the user above the tongue such that the mouthpiece 20 of the mouthpiece unit 10 is located at the teeth of the user. In this position, the inner ends of the upper and lower arms 22, 25 of the positioning mechanism 21 are located adjacent respective ones of the hard palate and the tongue of the user.

The user then grips the mouthpiece 20 by biting thereon. Through this biting action, the teeth or the gums, in this embodiment the teeth, act on the outer ends of the upper and lower arms 22, 25 of the positioning mechanism 21 against the biasing forces of the first and second biasing elements 24, 27, with the upper arm 22 being hinged about the pivot 23 such as to cause the outward movement of the inner end of the upper arm 22 to engage the hard palate and position the outlet unit 14 at a predetermined position relative to the inner end of the upper arm 22, and the lower arm 25 being hinged about the pivot 26 such as to cause the outward movement of the inner end of the lower arm 25 to space the inner end of the lower arm 25 from the outlet unit 14 and depress the tongue.

Figure 2B:
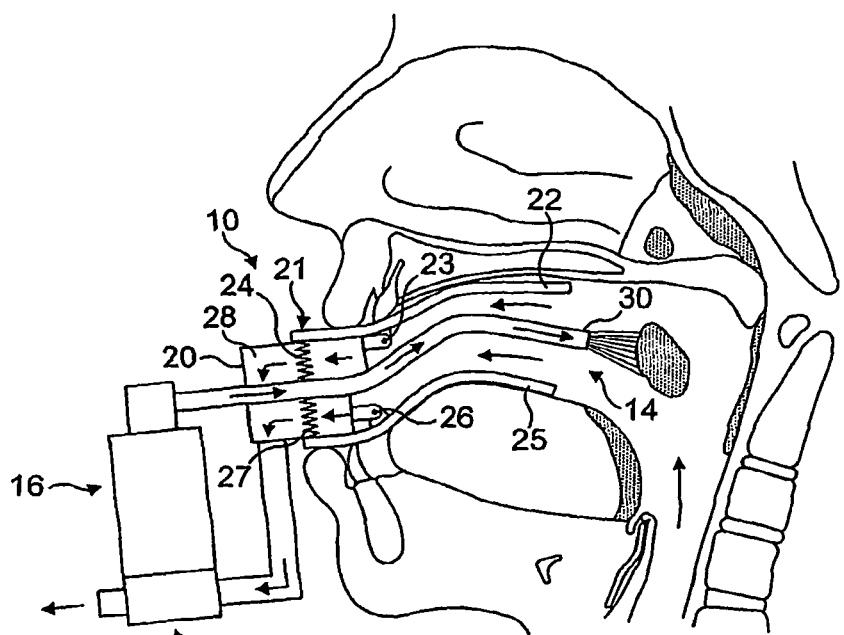

Referring to FIG. 2(b), the user then exhales through the mouthpiece 20, which exhalation causes the generation of a positive pressure in the oral cavity. This positive pressure acts both to maintain the depression of the tongue and close the oropharyngeal velum of the user.

In this embodiment, when the pressure developed at the mouthpiece 20 reaches a predetermined value, the trigger unit 18 is actuated to actuate the substance supply unit 16 to deliver a metered dose of substance to the at least one outlet 30 of the outlet unit 14, with the at least one outlet 30, where positioned by the positioning mechanism 21, delivering a focused spray onto the targeted mucosal surface.

It will be understood that the delivery device, in only delivering substance on the generation of a predetermined pressure in the oral cavity, is such that delivery is effected only when the oropharyngeal velum is closed, which thereby prevents delivered substance from entering the nasal cavity. Also, in this embodiment, in requiring an exhalation air flow during delivery, the inhalation of delivered substance is not possible. Indeed, any substance which is not delivered to the mucosal surface is expelled from the oral cavity by the exhalation air flow.

In one embodiment, where the delivery device is a single-dose device, the device can be discarded.

In another embodiment, where the delivery device is a multi-dose device, the device is ready for further use following priming of the substance supply unit 16.

In one embodiment, which finds particular application in relation to mass vaccination, the mouthpiece unit 10 and the outlet unit 14, as those components which include patient-contact surfaces, are replaceable, in a preferred embodiment as an integral unit, such as to provide a delivery system which provides for delivery to many subjects.

In one alternative embodiment the lower arm 25 and the associated second biasing element 27 of the positioning mechanism 21 could be omitted, with the generation of a positive pressure in the oral cavity acting to depress the tongue.

In another alternative embodiment the mouthpiece unit 10 can be configured to prevent actuation of the trigger unit 18 unless properly gripped in the mouth of the user. For example, in one embodiment the positioning mechanism 21 could be configured to prevent an air flow through the flow channel 28 in the mouthpiece 20, and thereby prevent actuation of the trigger unit 18, until the positioning mechanism 21 has been fully operated.

FIGS. 3(*a*) and (*b*) illustrate an exhalation breath-actuated delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the first-described embodiment only in that the outlet unit 14 includes a plurality of outlets 30, here first and second outlets 30*a*, 30*b* for delivering substance to mucosal surfaces of separate lymphoid structures, here a palatine tonsil and the lingual tonsil. In an alternative embodiment the delivery could be to the pair of palatine tonsils.

Operation of the delivery device of this embodiment is the same as for the above-described first embodiment.

FIGS. 4(*a*) and (*b*) illustrate an exhalation breath-actuated delivery device in accordance with a third embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the first-described embodiment only in that the upper arm 22 of the positioning mechanism 21 is fixed in the open position to the mouthpiece 20, with the first biasing element 24 being omitted.

With this configuration, the upper arm 22 of the positioning mechanism 21 is brought into engagement with the hard palate on the user closing his/her mouth, with the outlet unit 14 being positioned relative to the hard palate on such engagement. The lower arm 25 of the positioning mechanism 21 functions, as in the first-described embodiment, to depress the tongue.

Operation of the delivery device of this embodiment is the same as for the above-described first embodiment.

In one alternative embodiment the lower arm 25 and the associated second biasing element 27 of the positioning mechanism 21 could be omitted, with the generation of a positive pressure in the oral cavity acting to depress the tongue.

FIGS. 5(*a*) and (*b*) illustrate an exhalation breath-actuated delivery device in accordance with a fourth embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the first-described embodiment in that the flow channel 28 of the mouthpiece 20 is closed to the atmosphere and fluidly connected only to the trigger unit 18, such as to prevent an exhalation air flow therethrough on exhalation by the user, and the trigger unit 18 is configured to cause actuation of the substance supply unit 16 on generation of a predetermined pressure thereat.

Operation of the delivery device of this embodiment is the same as for the above-described first embodiment, with the generation of a positive pressure in the oral cavity as a result of attempted exhalation causing closure of the velum.

FIGS. 6(*a*) and (*b*) illustrate a delivery device in accordance with a fifth embodiment of the present invention.

The delivery device of this embodiment is quite similar in construction to the delivery device of the above-described first embodiment, and thus, in order to avoid unnecessary duplication of description, only the differences will be described in detail, with like reference signs designating like parts.

The delivery device of this embodiment differs from that of the first-described embodiment principally in that the mouthpiece 20 is not fluidly connected to the trigger unit 18, and the trigger unit 18 is manually actuatable to enable manual actuation of the substance supply unit 16. With this configuration, the substance supply unit 16 is actuated by manual actuation of the trigger unit 18 as opposed to breath actuation of the trigger unit 18.

In this embodiment the flow channel 28 is omitted from the mouthpiece 20 such that the mouthpiece 20 is closed, thus isolating the oral cavity from the atmosphere in operation of the delivery device. With this configuration, a positive pressure is developed in the oral cavity as a result of the user attempting to exhale, which positive pressure causes closure of the oropharyngeal velum of the user.

In an alternative embodiment, and similarly to the delivery device of the first-described embodiment, the mouthpiece 20 can include a flow channel 28 which communicates with the atmosphere. With this configuration, as in the delivery device of the first-described embodiment, a positive pressure is developed in the oral cavity as a result of the user exhaling through the mouthpiece 20, which positive pressure causes closure of the oropharyngeal velum of the user.

Operation of the delivery device of this embodiment is broadly the same as for the above-described first embodiment, with the user gripping the mouthpiece 20 by biting thereon and exhaling, or at least attempting to exhale, such as to generate a positive pressure in the oral cavity, but differs in that the user manually actuates the trigger unit 18 to cause actuation of the substance supply unit 16.

FIGS. 7(*a*) and (*b*) illustrate a delivery device in accordance with a sixth embodiment of the present invention.

The delivery device of this embodiment finds particular application with subjects who are unable to cooperate, such as infants or unconscious patients.

The delivery device comprises a mouthpiece unit 110 which is located in the mouth of a subject, an outlet unit 114 which extends through the mouthpiece unit 110 into the oral cavity of the subject and through which substance is delivered to mucosal surfaces of the oral cavity, a substance supply unit 116 for delivering metered doses of substance to the outlet unit 114, and a trigger unit 118 for actuating the substance supply unit 116.

In this embodiment the substance is a vaccine, but in alternative embodiments can be a medicament.

In this embodiment the mouthpiece unit 110 includes a sucking element 120, upon which the subject sucks when located in the oral cavity as a consequence of the reflex sucking action.

Figure 7A:
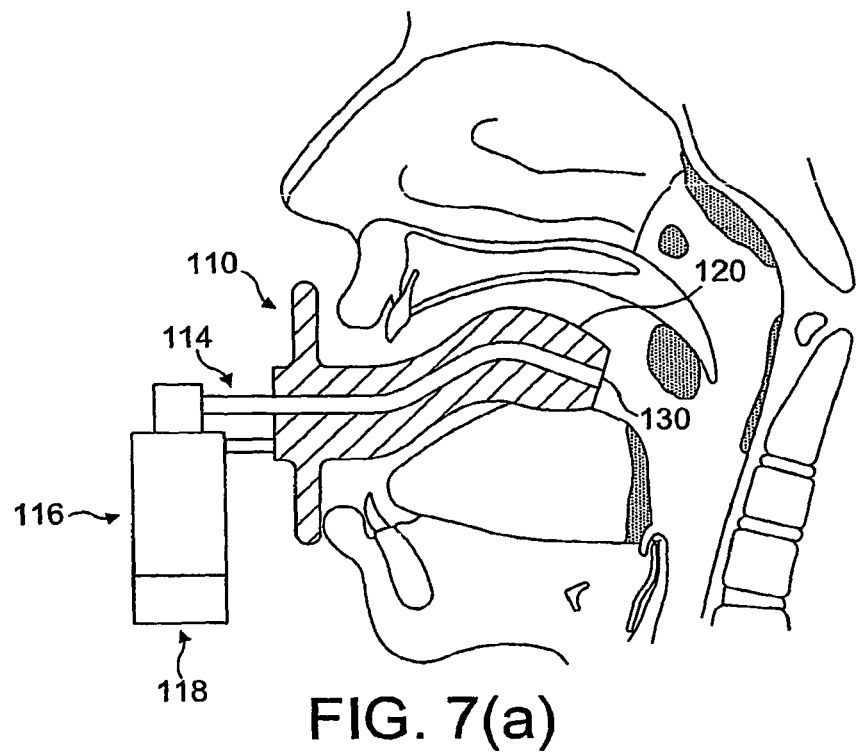
Figure 7B:
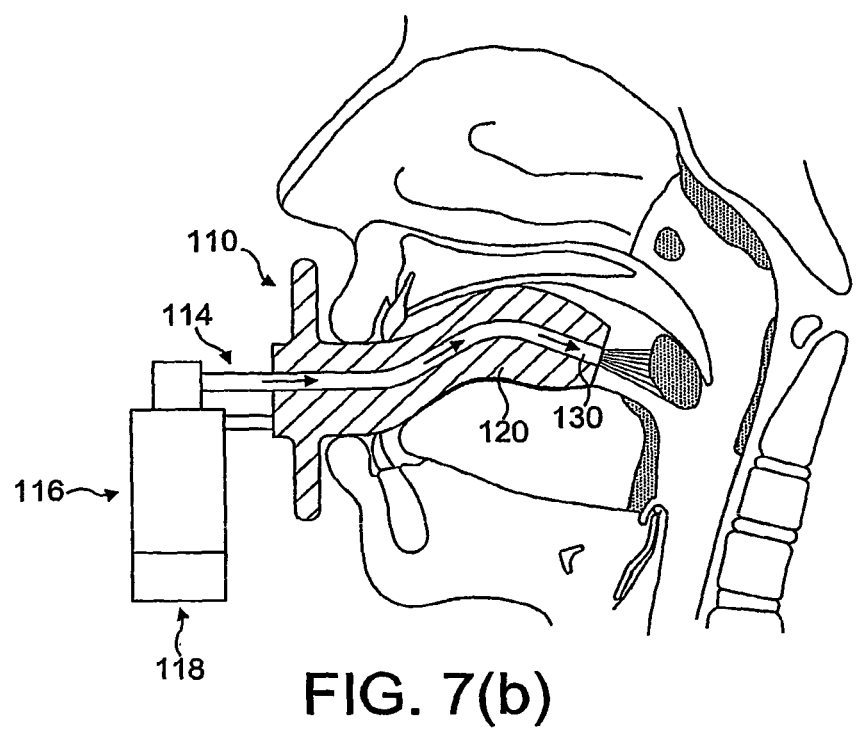

The sucking element 120, in this embodiment in the form of an elongate bulb member in the manner of a dummy or soother for an infant, is configured such as to adopt a position against the hard palate when sucked, as illustrated in FIG. 7(b), such as both to fix the position of the outlet unit 114 relative to the hard palate and depress the tongue, thereby directing the outlet unit 114 towards a targeted mucosal surface as will be described in more detail hereinbelow.

In this embodiment the outlet unit 114 includes at least one outlet 130, in this embodiment a single nozzle, for delivering substance at a targeted mucosal surface to the rear of the oral cavity, here of the palatine tonsils. The extent of the outlet unit 114 is configured to position the at least one outlet 130 thereof as far as possible to the rear of the oral cavity without causing discomfort or inducing the vomiting reflexes.

In this embodiment the at least one outlet 130 is configured to provide a focused spray onto the targeted mucosal surface. In an alternative embodiment the at least one outlet 130 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 116 comprises an aerosol canister for delivering metered doses of substance in a volume of propellant, preferably a hydrofluoroalkane (HFA) propellant or the like, which is fluidly connected to the outlet unit 114 to deliver substance from the at least one outlet 130 thereof.

In this embodiment the substance supply unit 116 is a multi-dose unit for delivering a plurality of metered doses of substance. In another embodiment the substance supply unit 116 could be a single-dose unit for delivering a single metered dose of substance.

The substance supply unit 116 is pre-primeable, in this embodiment by loading a resilient element, and is coupled to the trigger unit 118 such that, when the trigger unit 118 is actuated, the resilient element is released to actuate the substance supply unit 116 to deliver a metered dose of substance through the at least one outlet 130 as a focused spray.

In this embodiment the trigger unit 118 is manually actuated such as to enable actuation of the substance supply unit 116 by an operator.

In an alternative embodiment the substance supply unit 116 could comprise a mechanical delivery pump, in particular a liquid delivery pump or a powder delivery pump, which delivers metered doses of substance on actuation thereof. In one embodiment a syringe could be used as the delivery pump.

In another alternative embodiment the substance supply unit 116 could comprise a dry powder delivery unit which delivers metered doses of substance on actuation thereof.

Operation of the delivery device will now be described hereinbelow.

Referring to FIG. 7(a), the sucker element 120 of the mouthpiece unit 110 is first inserted into the oral cavity of the subject above the tongue such that the sucker element 120 is located between the tongue and the hard palate.

The subject then, as a result of the reflex sucking action, sucks on the sucker element 120 of the mouthpiece unit 110. Through this sucking action and the configuration of the sucker element 120, the position of the mouthpiece unit 110 is fixed in the oral cavity, such as both to reference the direction of the outlet unit 114 at a targeted mucosal surface by the sucker element 120 of the mouthpiece unit 110 acting on the hard palate, and cause the depression of the tongue which facilitates access to the rear of the oral cavity, in particular the mucosal surfaces of the lymphoid structures to the rear of the oral cavity.

Referring to FIG. 7(b), with the position of the mouthpiece unit 110 so fixed, the trigger unit 118 is then actuated by an operator to actuate the substance supply unit 116 to deliver a metered dose of substance to the at least one outlet 130 of the outlet unit 114, with the at least one outlet 130 delivering a focused spray onto the targeted mucosal surface.

With the above-described operation of the delivery device, the closure of the oropharyngeal velum of the subject cannot be ensured. In neonates, however, to which the delivery device has particular application, a flow stimulus, typically cold air, can be delivered to the region surrounding the eyes to cause a reflex action which elevates the oropharyngeal velum.

In one embodiment, where the delivery device is a single-dose device, the device can be discarded.

In another embodiment, where the delivery device is a multi-dose device, the device is ready for further use following priming of the substance supply unit 116.

In one embodiment, which finds particular application in relation to mass vaccination, the mouthpiece unit 110 and the outlet unit 114, as those components which include patient-contact surfaces, are replaceable, in a preferred embodiment as an integral unit, such as to provide a delivery system which provides for delivery to many subjects.

Figure 8A:
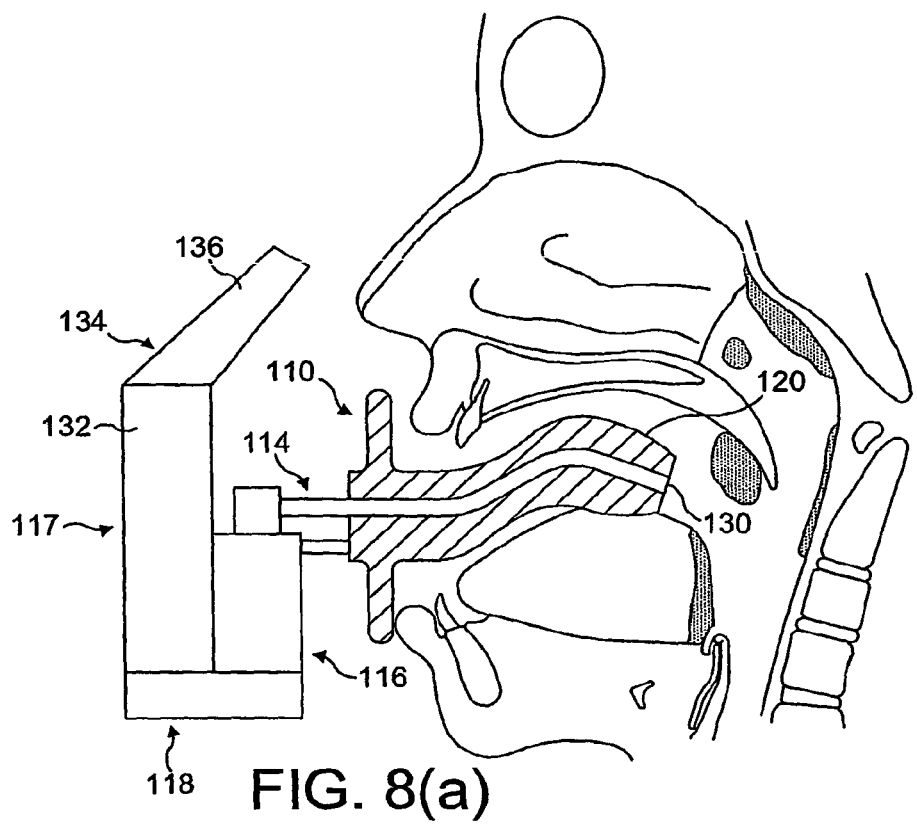
Figure 8B:
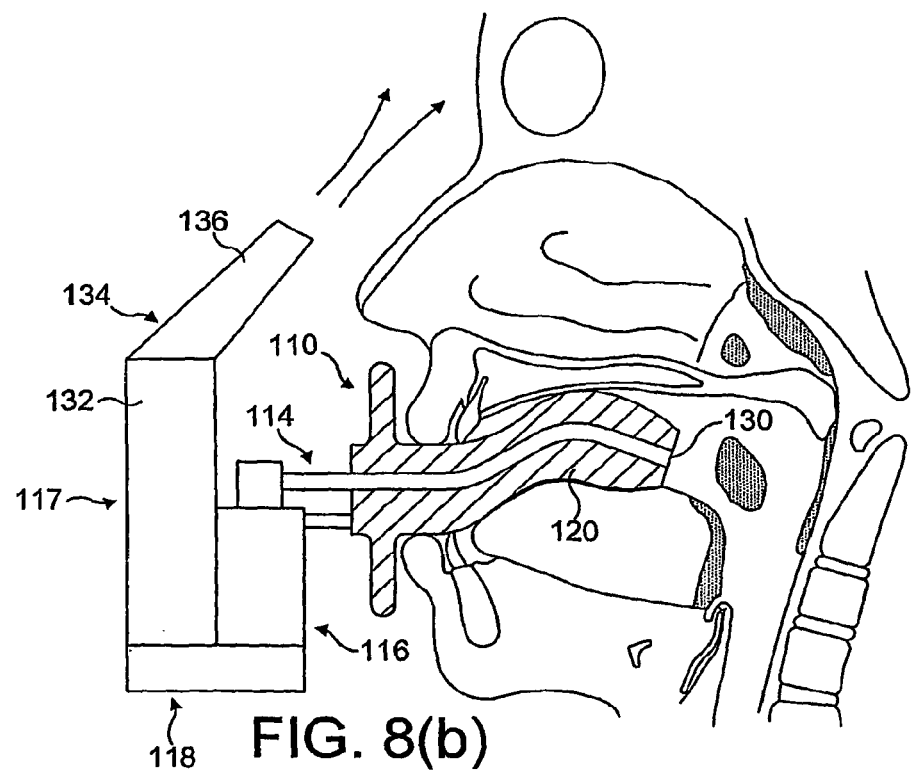
Figure 8C:
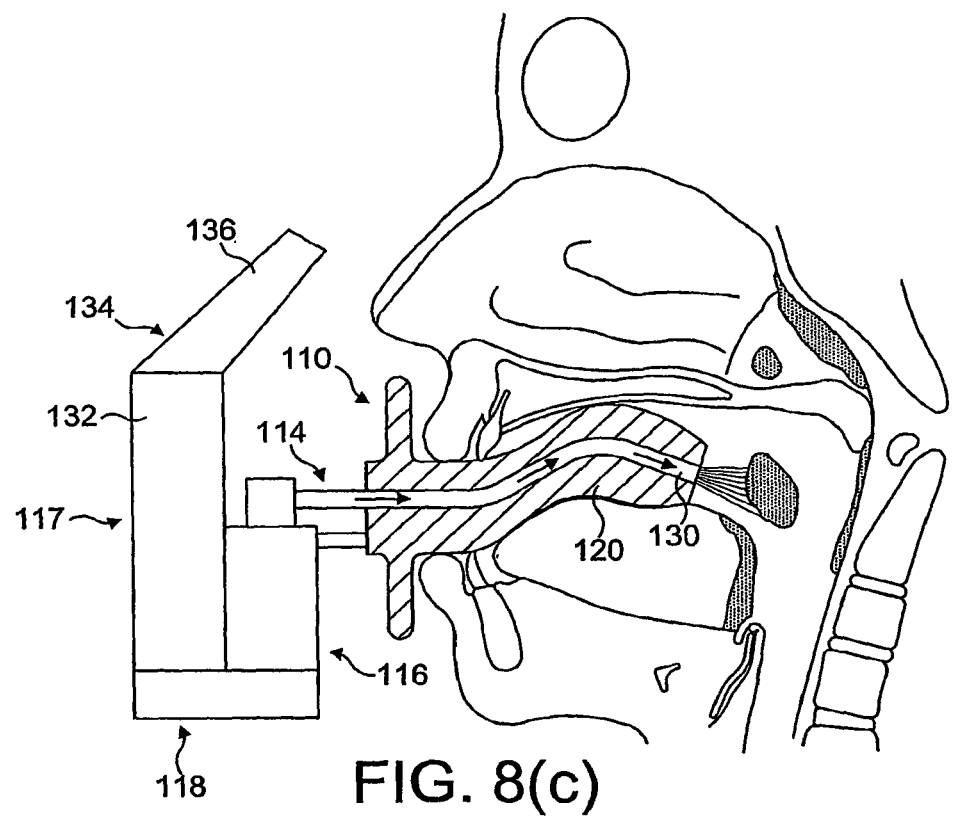

FIG. 8(a) to (c) illustrate a delivery device in accordance with a seventh embodiment of the present invention.

The delivery device of this embodiment finds particular application with subjects who are unable to cooperate; such as infants or patients.

The delivery device comprises a mouthpiece unit 110 which is located in the mouth of a subject, an outlet unit 114 which extends through the mouthpiece unit 110 into the oral cavity of the subject and through which substance is delivered to mucosal surfaces of the oral cavity, a substance supply unit 116 for delivering metered doses of substance to the outlet unit 114, a reflex fluid delivery unit 117 for delivering a reflex-inducing fluid, and a trigger unit 118 for actuating the substance supply unit 116 and the reflex fluid delivery unit 117.

In this embodiment the substance is a vaccine, but in alternative embodiments can be a medicament.

In this embodiment the mouthpiece unit 110 includes a sucking element 120, upon which the subject sucks when located in the oral cavity as a consequence of the reflex sucking action.

The sucking element 120, in this embodiment in the form of an elongate bulb member in the manner of a dummy or soother for an infant, is configured such as to adopt a position against the hard palate when sucked, as illustrated in FIG. 8(b), such as both to fix the position of the outlet unit 114 relative to the hard palate and depress the tongue, thereby directing the outlet unit 114 towards a targeted mucosal surface as will be described in more detail herein below.

In this embodiment the outlet unit 114 includes at least one outlet 130, in this embodiment a single nozzle, for delivering substance at a targeted mucosal surface to the rear of the oral cavity, here of the palatine tonsils. The extent of the outlet unit 114 is configured to position the at least one outlet 130 thereof as far as possible to the rear of the oral cavity without causing discomfort or inducing the vomiting reflexes.

In this embodiment the at least one outlet 130 is configured to provide a focused spray onto the targeted mucosal surface. In an alternative embodiment the at least one outlet 130 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 116 comprises an aerosol canister for delivering metered doses of substance in a volume of propellant, preferably a hydrofluoroalkane (HFA) propellant or the like, which is fluidly connected to the outlet unit 114 to deliver substance from the at least one outlet 130 thereof.

In this embodiment the substance supply unit 116 is a multi-dose unit for delivering a plurality of metered doses of substance. In another embodiment the substance supply unit 116 could be a single-dose unit for delivering a single metered dose of substance.

The substance supply unit 116 is pre-primeable, in this embodiment by loading a resilient element, and is coupled to the trigger unit 118 such that, when the trigger unit 118 is actuated, the resilient element is released to actuate the substance supply unit 116 to deliver a metered dose of substance through the at least one outlet 130 as a focused spray.

The reflex fluid delivery unit 117 is configured to deliver a reflex-inducing fluid, in this embodiment a gas, such as air, to the face of the subject, in this embodiment a region surrounding the eyes, prior to the delivery of substance to the oral cavity. The reflex fluid delivery unit 117 is coupled to the trigger unit 118 such as to be actuated at the onset, or just immediately prior, to the delivery of substance. The delivery of a fluid, typically a gas or water, to the face of a subject, particularly an infant, is such as to cause a reflex action, often referred to as the diving reflex, which causes the vocal chords to close off the larynx and elevation of the oropharyngeal velum. By co-ordinating this reflex action and the delivery of substance such that the reflex action is elicited at the onset of delivery, the inhalation of substance can be prevented and the transfer of substance to the nasal cavity can be at least substantially prevented. In providing for this reflex action, improved delivery to non-compliant subjects, who may not otherwise provide velum closure, can be achieved. Such subjects are typically infants, and also animal subjects. It is envisaged that the delivery device could also possibly be utilized with unconscious subjects, non-cooperating human subjects, typically epileptics or comatosed patients.

The reflex fluid delivery unit 117 comprises a reflex fluid supply unit 132 for supplying a volume of a reflex-inducing fluid, in this embodiment a gas, on actuation thereof, and a outlet unit 134 which is fluidly connected to the reflex fluid supply unit 132 such as to direct a flow of the supplied reflex-inducing fluid to the face of the subject, in this embodiment a region about the eyes of the subject.

In this embodiment the reflex fluid supply unit 132 comprises a pressurized canister which is actuatable to supply metered volumes of a gas.

In this embodiment the outlet unit 134 includes at least one outlet 136, here a single nozzle, for delivering a flow of the reflex-inducing fluid to the face of the subject, in this embodiment a region about the eyes of the subject.

In this embodiment the trigger unit 118 is manually actuated such as to enable actuation of the substance supply unit 116 and the reflex-fluid delivery unit 117 by an operator.

In an alternative embodiment the substance supply unit 116 could comprise a mechanical delivery pump, in particular a liquid delivery pump or a powder delivery pump, which delivers metered doses of substance on actuation thereof.

In another alternative embodiment the substance supply unit 116 could comprise a dry powder delivery unit which delivers metered doses of substance on actuation thereof.

Operation of the delivery device will now be described hereinbelow.

Referring to FIG. 8(a), the sucker element 120 of the mouthpiece unit 110 is first inserted into the oral cavity of the subject above the tongue such that the sucker element 120 is located between the tongue and the hard palate.

The subject then, as a result of the reflex sucking action, sucks on the sucker element 120 of the mouthpiece unit 110. Through this sucking action and the configuration of the sucker element 120, the position of the mouthpiece unit 110 is fixed in the oral cavity, such as both to reference the direction of the outlet unit 114 at a targeted mucosal surface by the sucker element 120 of the mouthpiece unit 110 acting on the hard palate, and cause the depression of the tongue which facilitates access to the rear of the oral cavity, in particular the mucosal surfaces of the lymphoid structures to the rear of the oral cavity.

With the position of the mouthpiece unit 110 so fixed, the trigger unit 118 is then actuated by an operator to actuate the reflex fluid delivery unit 117 to deliver a reflex-inducing fluid to the face of the subject such as to cause the diving reflex and the closure of the vocal chords against the larynx and elevation of the oropharyngeal velum, as illustrated in FIG. 8(b), and simultaneously actuate the substance supply unit 116 to deliver a metered dose of substance to the at least one outlet 130 of the outlet unit 114, as illustrated in FIG. 8(c), with the at least one outlet 130 delivering a focused spray onto the targeted mucosal surface.

In one embodiment, where the delivery device is a single-dose device, the device can be discarded.

In another embodiment, where the delivery device is a multi-dose device, the device is ready for further use following priming of the substance supply unit 116.

In one embodiment, which finds particular application in relation to mass vaccination, the mouthpiece unit 110 and the outlet unit 114, as those components which include patient-contact surfaces, are replaceable, in a preferred embodiment as an integral unit, such as to provide a delivery system which provides for delivery to many subjects.

Figure 9A:
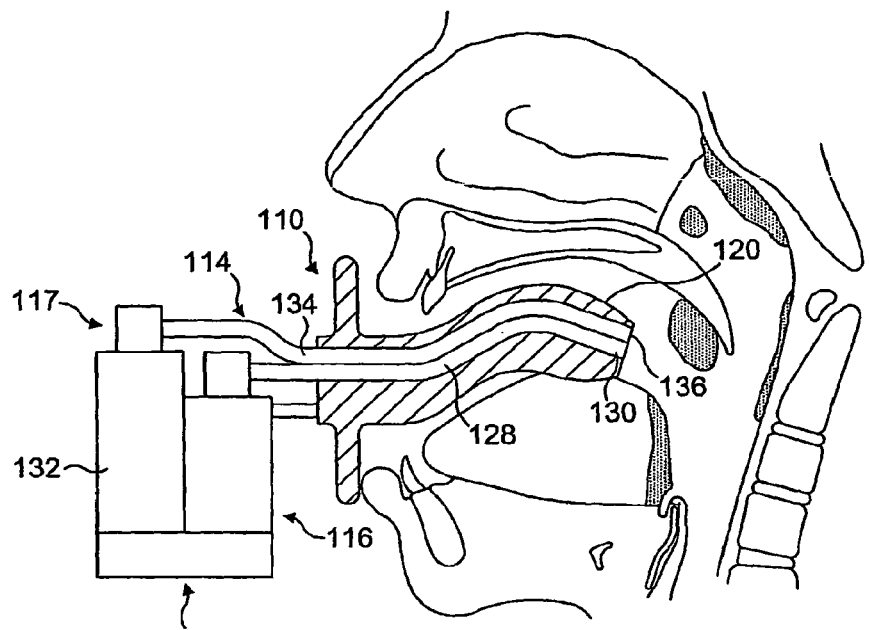
Figure 9B:
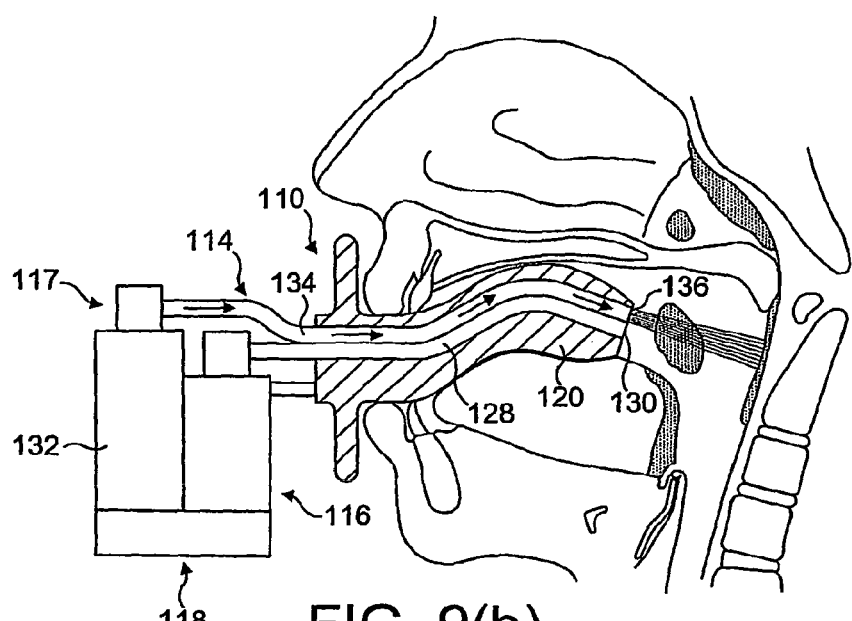
Figure 9C:
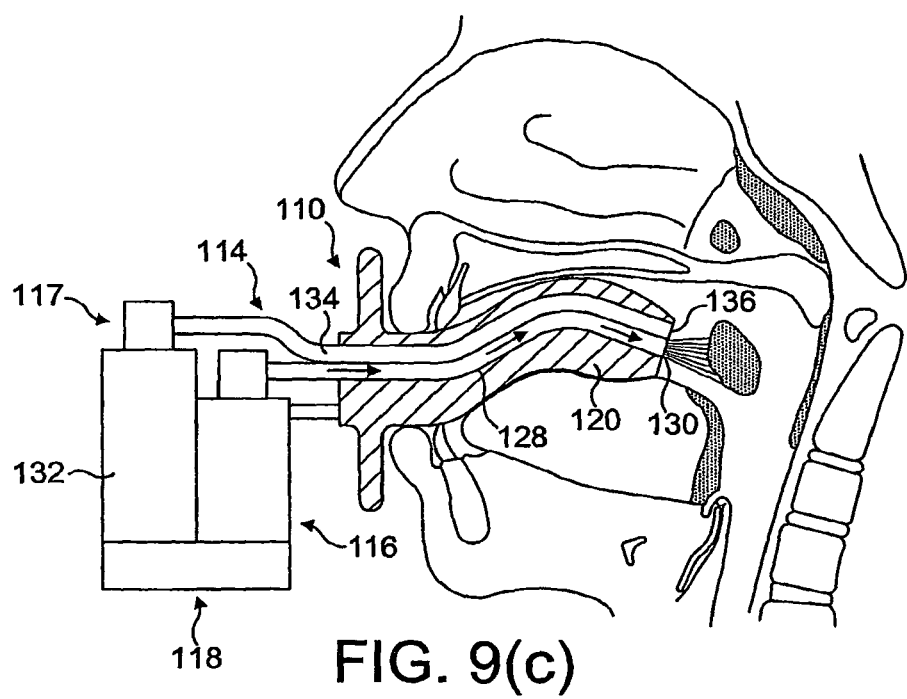

FIG. 9(a) to (c) illustrate a delivery device in accordance with an eighth embodiment of the present invention.

The delivery device of this embodiment finds particular application with subjects who are unable to cooperate, such as infants or unconscious patients.

The delivery device comprises a mouthpiece unit 110 which is located in the mouth of a subject, an outlet unit 114 which extends through the mouthpiece unit 110 into the oral cavity of the subject and through which substance is delivered to mucosal surfaces of the oral cavity and a reflex-inducing fluid is delivered into the oral cavity, a substance supply unit 116 for delivering metered doses of substance to the outlet unit 114, a reflex fluid supply unit 117 for delivering a reflex-inducing fluid to the outlet unit 114, and a trigger unit 118 for actuating the substance supply unit 116 and the reflex fluid supply unit 117.

In this embodiment the substance is a vaccine, but in alternative embodiments can be a medicament.

In this embodiment the mouthpiece unit 110 includes a sucking element 120, upon which the subject sucks when located in the oral cavity as a consequence of the reflex sucking action.

The sucking element 120, in this embodiment in the form of an elongate bulb member in the manner of a dummy or soother for an infant, is configured such as to adopt a position against the hard palate when sucked, as illustrated in FIG. 9(b), such as both to fix the position of the outlet unit 114 relative to the hard palate and depress the tongue, as will be described in more detail herein below.

In this embodiment the outlet unit 114 includes a first channel 128 which is fluidly connected to the substance supply unit 116 and includes at least one outlet 130, in this embodiment a single nozzle, for delivering substance at a targeted mucosal surface to the rear of the oral cavity, here of the palatine tonsils, and a second channel 134 which is fluidly connected to the reflex fluid supply unit 117 and includes at least one outlet 136, here a single nozzle, for delivering a reflex-inducing fluid, in this embodiment a gas, such as air, to the oral cavity of the subject, and in particular a posterior region of the oral cavity of the subject, in this embodiment the larynx. The extent of the outlet unit 114 is configured to position the at least one outlet 130 of the first channel 128 thereof as far as possible to the rear of the oral cavity without causing discomfort or inducing the vomiting reflexes.

In this embodiment the at least one outlet 130 of the first channel 128 is configured to provide a focused spray onto the targeted mucosal surface. In an alternative embodiment the at least one outlet 130 of the first channel 128 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 116 comprises an aerosol canister for delivering metered doses of substance in a volume of propellant, preferably a hydrofluoroalkane (HFA) propellant or the like, which is fluidly connected to the first channel 128 of the outlet unit 114 to deliver substance from the at least one outlet 130 thereof.

In this embodiment the substance supply unit 116 is a multi-dose unit for delivering a plurality of metered doses of substance. In another embodiment the substance supply unit 116 could be a single-dose unit for delivering a single metered dose of substance.

The substance supply unit 116 is pre-primeable, in this embodiment by loading a resilient element, and is coupled to the trigger unit 118 such that, when the trigger unit 118 is actuated, the resilient element is released to actuate the substance supply unit 116 to deliver a metered dose of substance through the at least one outlet 130 of the first channel 128 as a focused spray.

The reflex fluid supply unit 117 is configured to deliver a reflex-inducing fluid, in this embodiment a gas, such as air, to the oral cavity of the subject, and in particular a posterior region of the oral cavity of the subject, in this embodiment the larynx, prior to the delivery of substance to the oral cavity. The reflex fluid supply unit 117 is coupled to the trigger unit 118 such as to be actuated at the onset, or just immediately prior, to the delivery of substance. The delivery of a fluid, typically a gas or water, to the oral cavity of a subject, particularly an infant, is such as to cause a reflex action, often referred to as the diving reflex, which causes the vocal chords to close off the larynx and elevation of the oropharyngeal velum. By co-ordinating this reflex action and the delivery of substance such that the reflex action is elicited at the onset of delivery, the inhalation of substance can be prevented and the transfer of substance to the nasal cavity can be at least substantially prevented. In providing for this reflex action, improved delivery to non-compliant subjects, who may not otherwise provide velum closure, can be achieved. Such subjects are typically infants, and also animal subjects. It is envisaged that the delivery device could also possibly be utilized with unconscious subjects, non-cooperating human subjects, typically epileptics or comatosed patients.

In this embodiment the reflex fluid supply unit 117 comprises a pressurized canister which is actuatable to supply metered volumes of a gas.

In this embodiment the trigger unit 118 is manually actuated such as to enable actuation of the substance supply unit 116 and the reflex-fluid supply unit 117 by an operator.

In an alternative embodiment the substance supply unit 116 could comprise a mechanical delivery pump, in particular a liquid delivery pump or a powder delivery pump, which delivers metered doses of substance on actuation thereof.

In another alternative embodiment the substance supply unit 116 could comprise a dry powder delivery unit which delivers metered doses of substance on actuation thereof.

In one embodiment the substance supply unit 116 and the reflex-fluid supply unit 117 could be provided by a two-compartment syringe, where one compartment contains a metered amount of substance for delivery through the first, substance supply channel 128 and the other compartment contains a gas which is delivered as a gas flow through the second, reflex fluid supply channel 134.

Operation of the delivery device will now be described hereinbelow.

Referring to FIG. 9(a), the sucker element 120 of the mouthpiece unit 110 is first inserted into the oral cavity of the subject above the tongue such that the sucker element 120 is located between the tongue and the hard palate.

The subject then, as a result of the reflex sucking action, sucks on the sucker element 120 of the mouthpiece unit 110. Through this sucking action and the configuration of the sucker element 120, the position of the mouthpiece unit 110 is fixed in the oral cavity, such as both to reference the direction of the outlet unit 114 by the sucker element 120 of the mouthpiece unit 110 acting on the hard palate, and cause the depression of the tongue which facilitates access to the rear of the oral cavity, in particular the mucosal surfaces of the lymphoid structures to the rear of the oral cavity.

With the position of the mouthpiece unit 110 so fixed, the trigger unit 118 is then actuated by an operator to actuate the reflex fluid supply unit 117 to deliver a reflex-inducing fluid from the at least one outlet 136 of the second channel 134 of the outlet unit 114 to the posterior region of the oral cavity of the subject such as to cause the diving reflex and the closure of the vocal chords against the larynx and elevation of the oropharyngeal velum, as illustrated in FIG. 9(*b*), and simultaneously actuate the substance supply unit 116 to deliver a metered dose of substance to the at least one outlet 130 of the first channel 128 of the outlet unit 114, as illustrated in FIG. 9(*c*), with the at least one outlet 130 of the first channel 128 delivering a focused spray onto the targeted mucosal surface.

In one embodiment, where the delivery device is a single-dose device, the device can be discarded.

In another embodiment, where the delivery device is a multi-dose device, the device is ready for further use following priming of the substance supply unit 116.

In one embodiment, which finds particular application in relation to mass vaccination, the mouthpiece unit 110 and the outlet unit 114, as those components which include patient-contact surfaces, are replaceable, in a preferred embodiment as an integral unit, such as to provide a delivery system which provides for delivery to many subject.

FIGS. 10(*a*) and (*b*) illustrate a delivery device in accordance with a ninth embodiment of the present invention.

The delivery device of this embodiment finds particular application with subjects who are unable to cooperate, such as infants or unconscious patients.

The delivery device comprises a mouthpiece unit 210 which is located in the mouth of a subject, an outlet unit 214 which extends through the mouthpiece unit 210 into the oral cavity of the subject and through which substance is delivered to mucosal surfaces of the oral cavity, a substance supply unit 216 for delivering metered doses of substance to the outlet unit 214, and a trigger unit 218 for actuating the substance supply unit 216.

In this embodiment the substance is a vaccine, but in alternative embodiments can be a medicament.

In this embodiment the mouthpiece unit 210 includes a sucking element 220, upon which the subject sucks when located in the oral cavity as a consequence of the reflex sucking action.

The sucking element 220, in this embodiment in the form of an inflatable, elongate bulb member in the manner of a dummy or soother for an infant, is configured, when inflated and sucked by the subject, such as to adopt a position against the hard palate, as illustrated in FIG. 10(*b*), such as both to fix the position of the outlet unit 214 relative to the hard palate and depress the tongue, thereby directing the outlet unit 214 towards a targeted mucosal surface as will be described in more detail hereinbelow.

In this embodiment the outlet unit 214 includes at least one outlet 230, in this embodiment a single nozzle, for delivering substance at a targeted mucosal surface to the rear of the oral cavity, here of the palatine tonsils. The extent of the outlet unit 214 is configured to position the at least one outlet 230 thereof as far as possible to the rear of the oral cavity without causing discomfort or inducing the vomiting reflexes.

In this embodiment the at least one outlet 230 is configured to provide a focused spray onto the targeted mucosal surface. In an alternative embodiment the at least one outlet 230 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 216 comprises an aerosol canister for delivering metered doses of substance in a volume of propellant, preferably a hydrofluoroalkane (HFA) propellant or the like, which is fluidly connected to the outlet unit 214 to deliver substance from the at least one outlet 230 thereof.

In this embodiment the substance supply unit 216 is a multi-dose unit for delivering a plurality of metered doses of substance. In another embodiment the substance supply unit 216 could be a single-dose unit for delivering a single metered dose of substance.

The substance supply unit 216 is pre-primeable, in this embodiment by loading a resilient element, and is coupled to the trigger unit 218 such that, when the trigger unit 218 is actuated, the resilient element is released to actuate the substance supply unit 216 to deliver a metered dose of substance through the at least one outlet 230 as a focused spray.

In this embodiment the trigger unit 218 is manually actuated such as to enable actuation of the substance supply unit 216 by an operator.

In an alternative embodiment the substance supply unit 216 could comprise a mechanical delivery pump, in particular a liquid delivery pump or a powder delivery pump, which delivers metered doses of substance on actuation thereof.

In another alternative embodiment the substance supply unit 216 could comprise a dry powder delivery unit which delivers metered doses of substance on actuation thereof.

The delivery device further comprises an inflation unit 240 which is fluidly connected to the sucker element 220 and actuatable to inflate the sucker element 220 from a deflated, insertion configuration, as illustrated in FIG. 10(*a*), to an inflated, positioning configuration, as illustrated in FIG. 10(*b*).

In this embodiment the inflation unit 240 comprises a manually-actuatable balloon member 241 which delivers a predetermined volume of a contained gas into the sucker element 220 on compression of the same, as illustrated in FIG. 10(*b*), such as to inflate the sucker element 220 to the positioning configuration. In this embodiment the balloon member 241 is resiliently-biased such as to expand on release of the compressive, actuating force, which expansion of the balloon member 241 withdraws the volume of the contained gas from the sucker element 220 and contracts the same to the insertion configuration.

In an alternative embodiment the inflation unit 240 could comprise a pre-primed unit or a pump unit, such as an electrically-operated pump unit, for delivering a predetermined volume of gas to inflate the sucker element 220 to the positioning configuration. In one embodiment the same pre-primed unit or pump unit could be utilized to deflate the sucker element 220 to the insertion configuration.

Operation of the delivery device will now be described hereinbelow.

Referring to FIG. 10(*a*), the sucker element 220 of the mouthpiece unit 210 is first inserted into the oral cavity of the subject above the tongue such that the sucker element 220 is located between the tongue and the hard palate.

As illustrated in FIG. 10(*b*), the inflation unit 240 is then actuated by compressing the balloon member 241 thereof such as to drive a predetermined volume of a contained gas into the sucker element 220 and cause the expansion of the same to the positioning configuration.

The subject then, as a result of the reflex sucking action, starts to suck on the sucker element 220 of the mouthpiece unit 210. Through this sucking action and the configuration of the inflated sucker element 220, the position of the mouthpiece unit 210 is fixed in the oral cavity, such as both to reference the direction of the outlet unit 214 at a targeted mucosal surface by the sucker element 220 acting on the hard palate, and cause the depression of the tongue which facilitates access to the rear of the oral cavity, in particular the mucosal surfaces of the lymphoid structures to the rear of the oral cavity.

Referring again to FIG. 10(b), with the position of the mouthpiece unit 210 so fixed, the trigger unit 218 is then actuated by an operator to actuate the substance supply unit 216 to deliver a metered dose of substance to the at least one outlet 230 of the outlet unit 214, with the at least one outlet 230 delivering a focused spray onto the targeted mucosal surface.

With the above-described operation of the delivery device, the closure of the oropharyngeal velum of the subject cannot be ensured. In neonates, however, to which the delivery device has particular application, a flow stimulus, typically cold air, can be delivered to the region surrounding the eyes to cause a reflex action which elevates the oropharyngeal velum.

In one embodiment, where the delivery device is a single-dose device, the device can be discarded.

In another embodiment, where the delivery device is a multi-dose device, the device is ready for further use following priming of the substance supply unit 216.

In one embodiment, which finds particular application in relation to mass vaccination, the mouthpiece unit 210 and the outlet unit 214, as those components which include patient-contact surfaces, are replaceable, in a preferred embodiment as an integral unit, such as to provide a delivery system which provides for delivery to many subjects.

Figure 11A:
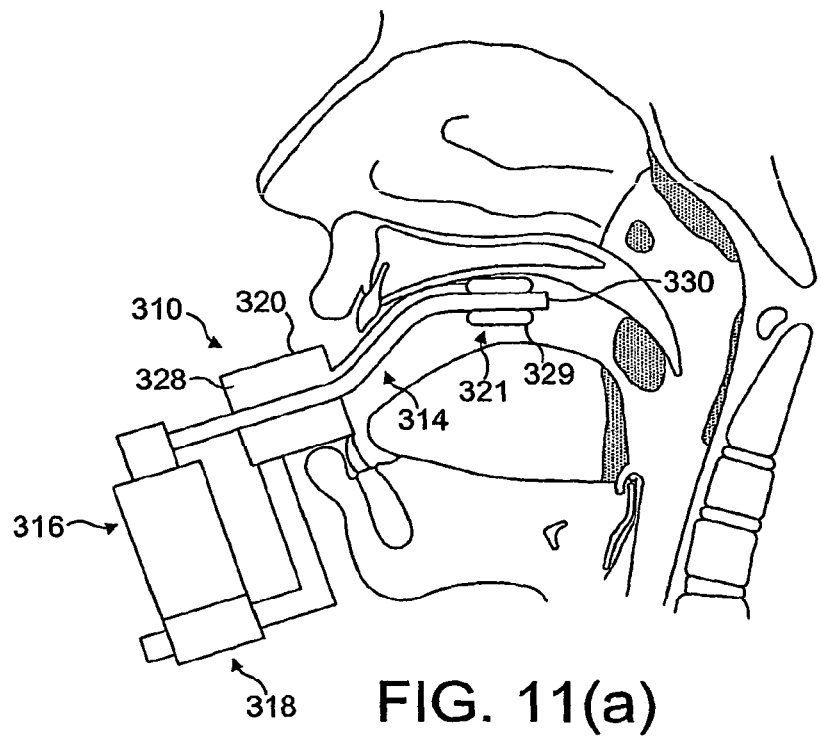

FIGS. 11(a) and (b) illustrate an exhalation breath-actuated delivery device in accordance with a tenth embodiment of the present invention.

The delivery device comprises a mouthpiece unit 310 which is gripped in the mouth of a user and through which the user exhales to actuate the delivery device, an outlet unit 314 which extends into the oral cavity of the user and through which substance is delivered to mucosal surfaces of the oral cavity, a substance supply unit 316 for delivering metered doses of substance to the outlet unit 314, and a breath-actuated trigger unit 318 for actuating the substance supply unit 316 in response to exhalation by the user.

In this embodiment the substance is a vaccine, but in alternative embodiments can be a medicament.

The mouthpiece unit 310 includes a mouthpiece 320 which is configured to be gripped between the teeth or gums of the user on the user biting thereon, with the lips of the user providing a seal to the mouthpiece 320, and a positioning mechanism 321 which acts both to fix the position of the outlet unit 314 relative to the hard palate and depress the tongue, thereby directing the outlet unit 314 towards a targeted mucosal surface as will be described in more detail hereinbelow.

In this embodiment the mouthpiece 320 includes a flow channel 328 through which an air flow generated on exhalation by the user is directed. The flow channel 328 is configured to provide a flow resistance to an exhalation air flow which is such as to generate a positive pressure in the oral cavity. This positive pressure is such as to cause closure of the oropharyngeal velum of the user, thereby isolating the oral cavity from the nasal cavity, and preventing the communication of substance to the nasal cavity where delivered to the oral cavity. The present inventor has also identified that this positive pressure acts to cause depression of the tongue which facilitates access to the mucosal surfaces of the lymphoid structures to the rear of the oral cavity. In one embodiment the mouthpiece 320 can include a collection element, typically a filter, to collect the delivered substance which is entrained by the exhalation breath and delivered therethrough.

Figure 11B:
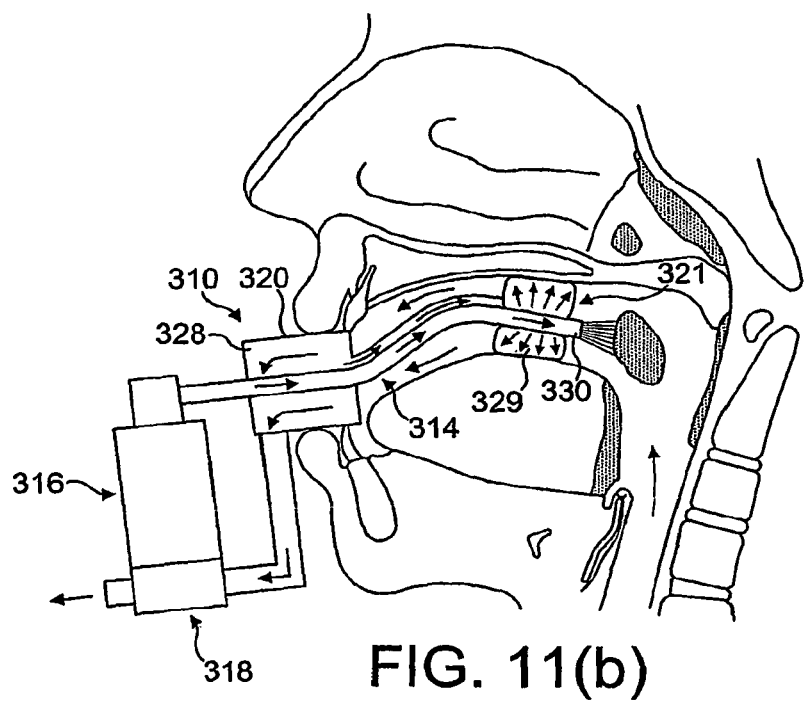

The positioning mechanism 321 comprises at least one expandable cuff member 329 which is disposed to the inner end of the outlet unit 314. As illustrated in FIG. 11(b), the at least one cuff member 329 is configured such as, on expansion, to space the outlet unit 314 by a predetermined distance from the hard palate, which is a fixed point of reference, and thereby provides that the outlet unit 314 is directed to a targeted mucosal surface, and also acts to depress the tongue so as to facilitate access to the rear of the oral cavity. In this embodiment the at least one cuff member 329 comprises an inflatable member.

In this embodiment the at least one cuff member 329 is in fluid communication with the mouthpiece 320 of the mouthpiece unit 310, whereby the air flow generated by the user on exhalation through the mouthpiece 320 acts to inflate the at least one cuff member 329.

In an alternative embodiment the delivery device could include a separate inflation unit for inflating the at least one cuff member 329 subsequent to insertion of the outlet unit 314 into the oral cavity, and in a preferred embodiment subsequent to, preferably in response to, exhalation through the mouthpiece 320.

In this embodiment the at least one cuff member 329 comprises a flexible balloon element which is inflated on exhalation through the mouthpiece 320, with the at least one cuff member 329 deflating on the user ceasing exhalation. In the alternative embodiment, where the at least one cuff member 329 is inflated by a separate inflation unit, the at least one cuff member 329 could be deflated by the evacuation of gas therefrom using the same unit.

In one embodiment the at least one cuff member 329 could comprise a resilient balloon element which is inflated by the generation of a pressure at the mouthpiece 320, with the at least one cuff member 329 returning to the original, deflated configuration on the user ceasing to exhale through the mouthpiece 320.

In this embodiment the at least one cuff member 329 comprises a single annular cuff member 329 which is located about the outlet unit 314. In an alternative embodiment the at least one cuff member 329 could comprise a plurality of cuff members 329.

In alternative embodiments the at least one cuff member 329 could be configured such as to engage only one of either the hard palate in referencing the position of the outlet unit 314 or the tongue in depressing the same.

Through the provision of the positioning mechanism 321, exhalation by the user through the mouthpiece 320 acts to reference the direction of the outlet unit 314 at a targeted mucosal surface by the at least one cuff member 329 acting on the hard palate, and causes the depression of the tongue which facilitates access to the rear of the oral cavity, in particular the mucosal surfaces of the lymphoid structures to the rear of the oral cavity. As already mentioned hereinabove, and illustrated in FIG. 1, the tongue ordinarily rests close to the hard palate and thereby obstructs direct access to the mucosal surfaces of the lymphoid structures in the oral cavity, notably the palatine tonsils and the lingual tonsil.

In this embodiment the outlet unit 314 includes at least one outlet 330, in this embodiment a single nozzle, for delivering substance at a targeted mucosal surface to the rear of the oral cavity, here of the palatine tonsils. The extent of the outlet unit 314 is configured to position the at least one outlet 330 thereof as far as possible to the rear of the oral cavity without causing discomfort or inducing the vomiting reflexes.

In this embodiment the at least one outlet 330 is configured to provide a focused spray onto the targeted mucosal surface. In an alternative embodiment the at least one outlet 330 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 316 comprises an aerosol canister for delivering metered doses of substance in a volume of propellant, preferably a hydrofluoroalkane (HFA) propellant or the like, which is fluidly connected to the outlet unit 314 to deliver substance from the at least one outlet 330 thereof.

In this embodiment the substance supply unit 316 is a multi-dose unit for delivering a plurality of metered doses of substance. In another embodiment the substance supply unit 316 could be a single-dose unit for delivering a single metered dose of substance. In this embodiment the substance supply unit 316 and the trigger unit 318 could be configured such as in use to be located within the oral cavity, with the mouthpiece unit 310 including a shield, much in the manner of a dummy or soother for an infant, to prevent any possibility of the device being swallowed. This embodiment lends itself to fabrication from inexpensive plastics, and in particular bio-degradable materials.

The substance supply unit 316 is pre-primeable, in this embodiment by loading a resilient element, and is coupled to the trigger unit 318 such that, when the trigger unit 318 is actuated by the exhalation breath of the user, the resilient element is released to actuate the substance supply unit 316 to deliver a metered dose of substance through the at least one outlet 330 as a focused spray.

In this embodiment the trigger unit 318 is configured to cause actuation of the substance supply unit 316 on generation of a predetermined pressure thereat.

In an alternative embodiment the trigger unit 318 could be configured to cause actuation of the substance supply unit 316 on generation of a predetermined flow rate therethrough.

In an alternative embodiment the substance supply unit 316 could comprise a mechanical delivery pump, in particular a liquid delivery pump or a powder delivery pump, which delivers metered doses of substance on actuation thereof.

In another alternative embodiment the substance supply unit 316 could comprise a dry powder delivery unit which delivers metered doses of substance on actuation thereof.

Operation of the delivery device will now be described hereinbelow.

Referring to FIG. 11(a), the outlet unit 314 is first inserted into the oral cavity of the user above the tongue such that the mouthpiece 320 of the mouthpiece unit 310 is located at the teeth of the user.

The user then grips the mouthpiece 320 by biting thereon. Through this biting action, the teeth or the gums, in this embodiment the teeth, act to position the delivery device within the oral cavity, and in particular position the outlet unit 314 within the oral cavity.

Referring to FIG. 11(b), the user then exhales through the mouthpiece 320, which exhalation causes the generation of a positive pressure in the oral cavity. This positive pressure acts to close the oropharyngeal velum of the user and inflate the at least one cuff member 329 of the positioning mechanism 321, such as both to reference the direction of the outlet unit 314 at a targeted mucosal surface by the at least one cuff member 329 acting on the hard palate, and cause the depression of the tongue by the at least one cuff member 329 acting thereon, which depression of the tongue facilitates access to the rear of the oral cavity, in particular the mucosal surfaces of the lymphoid structures to the rear of the oral cavity.

In this embodiment, when the pressure developed at the mouthpiece 320 reaches a predetermined value, the trigger unit 318 is actuated to actuate the substance supply unit 316 to deliver a metered dose of substance to the at least one outlet 330 of the outlet unit 314, with the at least one outlet 330, where positioned by the positioning mechanism 321, delivering a focused spray onto the targeted mucosal surface.

It will be understood that the delivery device, in only delivering substance on the generation of a predetermined pressure in the oral cavity, is such that delivery is effected only when the oropharyngeal velum is closed, which thereby prevents delivered substance from entering the nasal cavity. Also, in this embodiment, in requiring an exhalation air flow during delivery, the inhalation of delivered substance is not possible. Indeed, any substance which is not delivered to the mucosal surface is expelled from the oral cavity by the exhalation air flow.

In one embodiment, where the delivery device is a single-dose device, the device can be discarded.

In another embodiment, where the delivery device is a multi-dose device, the device is ready for further use following priming of the substance supply unit 316.

In one embodiment, which finds particular application in relation to mass vaccination, the mouthpiece unit 310 and the outlet unit 314, as those components which include patient-contact surfaces, are replaceable, in a preferred embodiment as an integral unit, such as to provide a delivery system which provides for delivery to many subjects.

In one alternative embodiment the at least one cuff member 329 of the positioning mechanism 321 could be configured to engage only the hard palate, with the generation of a positive pressure in the oral cavity acting to depress the tongue.

Figure 12A:
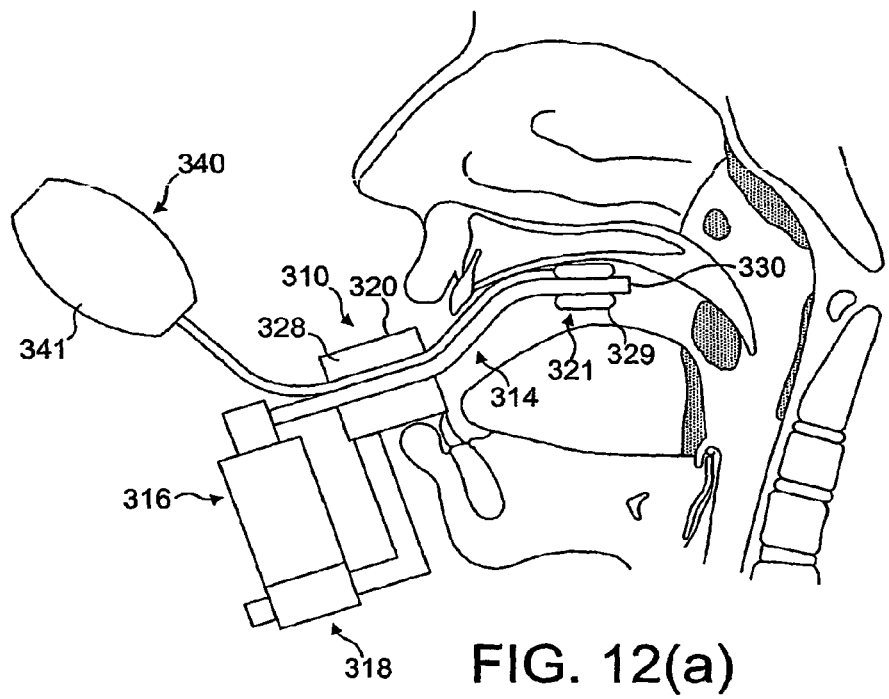

FIGS. 12(a) and (b) illustrate a delivery device in accordance with an eleventh embodiment of the present invention.

The delivery device of this embodiment is quite similar in construction to the delivery device of the above-described tenth embodiment, and thus, in order to avoid unnecessary duplication of description, only the differences will be described in detail, with like reference signs designating like parts.

Figure 12B:
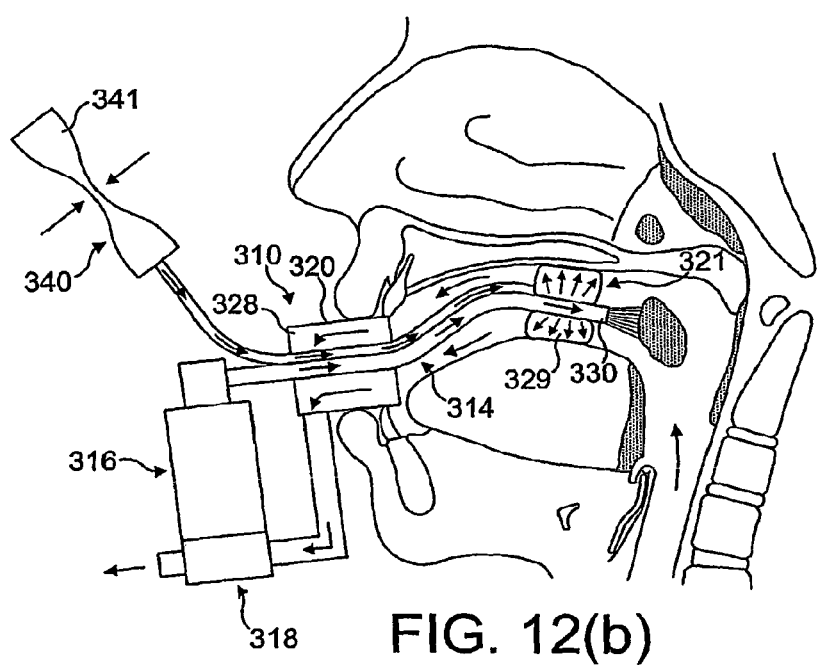

The delivery device of this embodiment differs from that of the tenth-described embodiment principally in that the mouthpiece 320 is not fluidly connected to the at least one cuff member 329 of the positioning mechanism 321, and in further comprising an inflation unit 340 which is fluidly connected to the at least one cuff member 329 and actuatable to inflate the at least one cuff member 329 from a deflated, insertion configuration, as illustrated in FIG. 12(a), to an inflated, positioning configuration, as illustrated in FIG. 12(b).

In this embodiment the inflation unit 340 comprises a manually-actuatable balloon member 341 which delivers a predetermined volume of a contained gas into the at least one cuff member 329 on compression of the same, as illustrated in FIG. 12(b), such as to inflate the at least one cuff member 329 to the positioning configuration. In this embodiment the balloon member 341 is resiliently-biased such as to expand on release of the compressive, actuating force, which expansion of the balloon member 341 withdraws the volume of the contained gas from the at least one cuff member 329 and contracts the same to the insertion configuration.

In an alternative embodiment the inflation unit 340 could comprise a pre-primed unit or a pump unit, such as an electrically-operated pump unit, for delivering a predetermined volume of gas to inflate the at least one cuff member 329. In one embodiment the same pre-primed unit or pump unit could be utilized to deflate the at least one cuff member 329 to the insertion configuration.

Operation of the delivery device of this embodiment is broadly the same as for the above-described tenth embodiment, with the user gripping the mouthpiece 320 by biting thereon and exhaling such as to generate a positive pressure in the oral cavity, but differs in that, prior to exhaling through the mouthpiece 320, the user actuates the inflation unit 340 such as to drive a predetermined volume of a contained gas into the at least one cuff member 329 and cause the expansion of the same to the positioning configuration.

FIGS. 13(*a*) and (*b*) illustrate an exhalation breath-actuated delivery device in accordance with a twelfth embodiment of the present invention.

The delivery device comprises a mouthpiece unit 410 which is gripped in the mouth of a user and through which the user exhales to actuate the delivery device, an outlet unit 414 which extends into the oral cavity of the user and through which substance is delivered to mucosal surfaces of the oral cavity, a substance supply unit 416 for delivering metered doses of substance to the outlet unit 414, and a breath-actuated trigger unit 418 for actuating the substance supply unit 416 in response to exhalation by the user.

In this embodiment the substance is a vaccine, but in alternative embodiments can be a medicament.

The mouthpiece unit 410 includes a mouthpiece 420 which is configured to be gripped between the teeth or gums of the user on the user biting thereon such as to fix the position of the outlet unit 414 within the oral cavity, thereby directing the outlet unit 414 towards a targeted mucosal surface as will be described in more detail hereinbelow, with the lips of the user providing a seal to the mouthpiece 420.

In this embodiment the mouthpiece 420 includes a flow channel 428 through which an air flow generated on exhalation by the user is directed. The flow channel 428 is configured to provide a flow resistance to an exhalation air flow which is such as to generate a positive pressure in the oral cavity. This positive pressure is such as to cause closure of the oropharyngeal velum of the user, thereby isolating the oral cavity from the nasal cavity, and preventing the communication of substance to the nasal cavity where delivered to the oral cavity. The present inventor has also identified that this positive pressure acts to cause depression of the tongue which facilitates access to the mucosal surfaces of the lymphoid structures to the rear of the oral cavity. In one embodiment the mouthpiece 420 can include a collection element, typically a filter, to collect the delivered substance which is entrained by the exhalation breath and delivered therethrough.

In this embodiment the outlet unit 414 includes at least one outlet 430, in this embodiment a single nozzle, for delivering substance at a targeted mucosal surface to the rear of the oral cavity, here of the palatine tonsils. The extent of the outlet unit 414 is configured to position the at least one outlet 430 thereof as far as possible to the rear of the oral cavity without causing discomfort or inducing the vomiting reflexes.

In this embodiment the at least one outlet 430 is configured to provide a focused spray onto the targeted mucosal surface. In an alternative embodiment the at least one outlet 430 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance supply unit 416 comprises an aerosol canister for delivering metered doses of substance in a volume of propellant, preferably a hydrofluoroalkane (HFA) propellant or the like, which is fluidly connected to the outlet unit 414 to deliver substance from the at least one outlet 430 thereof.

In this embodiment the substance supply unit 416 is a multi-dose unit for delivering a plurality of metered doses of substance. In another embodiment the substance supply unit 416 could be a single-dose unit for delivering a single metered dose of substance. In this embodiment the substance supply unit 416 and the trigger unit 418 could be configured such as in use to be located within the oral cavity, with the mouthpiece unit 420 including a shield, much in the manner of a dummy or soother for an infant, to prevent any possibility of the device being swallowed. This embodiment lends itself to fabrication from inexpensive plastics, and in particular bio-degradable materials.

The substance supply unit 416 is pre-primeable, in this embodiment by loading a resilient element, and is coupled to the trigger unit 418 such that, when the trigger unit 418 is actuated by the exhalation breath of the user, the resilient element is released to actuate the substance supply unit 416 to deliver a metered dose of substance through the at least one outlet 430 as a focused spray.

In this embodiment the trigger unit 418 is configured to cause actuation of the substance supply unit 416 on generation of a predetermined pressure thereat.

In an alternative embodiment the trigger unit 418 could be configured to cause actuation of the substance supply unit 416 on generation of a predetermined air flow therethrough.

In an alternative embodiment the substance supply unit 416 could comprise a mechanical delivery pump, in particular a liquid delivery pump or a powder delivery pump, which delivers metered doses of substance on actuation thereof.

In another alternative embodiment the substance supply unit 416 could comprise a dry powder delivery unit which delivers metered doses of substance on actuation thereof.

Operation of the delivery device will now be described hereinbelow.

Referring to FIG. 13(*a*), the outlet unit 414 is first inserted into the oral cavity of the user above the tongue such that the mouthpiece 420 of the mouthpiece unit 410 is located at the teeth of the user.

The user then grips the mouthpiece 420 by biting thereon. Through this biting action, the teeth or the gums, in this embodiment the teeth, act to position the delivery device within the oral cavity, and in particular position the outlet unit 414 within the oral cavity.

Referring to FIG. 13(*b*), the user then exhales through the mouthpiece 420, which exhalation causes the generation of a positive pressure in the oral cavity. This positive pressure acts to close the oropharyngeal velum of the user, and cause the depression of the tongue which facilitates access to the rear of the oral cavity, in particular the mucosal surfaces of the lymphoid structures to the rear of the oral cavity.

In this embodiment, when the pressure developed at the mouthpiece 420 reaches a predetermined value, the trigger unit 418 is actuated to actuate the substance supply unit 416 to deliver a metered dose of substance to the at least one outlet 430 of the outlet unit 414, with the at least one outlet 430 delivering a focused spray onto the targeted mucosal surface.

It will be understood that the delivery device, in only delivering substance on the generation of a predetermined pressure in the oral cavity, is such that delivery is effected only when the oropharyngeal velum is closed, which thereby prevents delivered substance from entering the nasal cavity. Also, in this embodiment, in requiring an exhalation air flow during delivery, the inhalation of delivered substance is not possible. Indeed, any substance which is not delivered to the mucosal surface is expelled from the oral cavity by the exhalation air flow.

In one embodiment, where the delivery device is a single-dose device, the device can be discarded.

In another embodiment, where the delivery device is a multi-dose device, the device is ready for further use following priming of the substance supply unit 416.

In one embodiment, which finds particular application in relation to mass vaccination, the mouthpiece unit 410 and the outlet unit 414, as those components which include patient-contact surfaces, are replaceable, in a preferred embodiment as an integral unit, such as to provide a delivery system which provides for delivery to many subjects.

FIGS. 14(a) and (b) illustrate a breath-actuated delivery device in accordance with a thirteenth embodiment of the present invention.

The delivery device comprises a mouthpiece unit 510 which is gripped in the mouth of a user and through which the user exhales to actuate the delivery device, a nosepiece unit 512 which is fitted to one nostril of the user, a first outlet unit 514 which extends into the oral cavity of the user and through which substance is delivered to mucosal surfaces in the oral cavity, a second outlet unit 516 which extends into the nasal cavity of the user and through which substance is delivered to mucosal surfaces in the nasal cavity, and a delivery unit 518 for delivering substance to the first and second outlet units 514, 516 in response to exhalation by the user.

The mouthpiece unit 510 includes a mouthpiece 520 which is configured to be gripped between the teeth or gums of the user on the user biting thereon, such as to fix the position of the first outlet unit 514 within the oral cavity, thereby directing the first outlet unit 514 towards a targeted mucosal surface as will be described in more detail hereinbelow, with the lips of the user providing a seal to the mouthpiece 520.

In this embodiment the mouthpiece 520 includes a flow channel 522 through which an air flow generated on exhalation by the user is directed. The flow channel 522 is configured to provide a flow resistance to an exhalation air flow which is such as to generate a positive pressure in the oral cavity. This positive pressure is such as to cause closure of the oropharyngeal velum of the user, thereby isolating the oral cavity from the nasal cavity, and preventing the communication of substance to the nasal cavity where delivered to the oral cavity. As mentioned hereinabove, the present inventor has also identified that this positive pressure acts to cause the depression of the tongue which facilitates access to the mucosal surfaces to the rear of the oral cavity.

The nosepiece unit 512 includes a nosepiece 524 which provides a sealing fit with the nares of the one nostril. In this embodiment the nosepiece 524 is shaped such that, on fitting in the one nostril, the nosepiece 524 adopts a fixed position such as to direct the second outlet unit 516 at a targeted mucosal surface to the rear of the nasal cavity, here of the adenoids.

In this embodiment the first outlet unit 514 includes at least one outlet 526, in this embodiment a single nozzle, for delivering substance at a targeted mucosal surface to the rear of the oral cavity, here of a palatine tonsil. In another embodiment the at least one outlet 526 could be configured to target the lingual tonsil or the pharyngeal tissue.

In this embodiment the at least one outlet 526 is configured to provide a focused spray onto the targeted mucosal surface. In an alternative embodiment the at least one outlet 526 can be configured to provide a focused spray of particles which have a dimension and velocity such as to penetrate the mucosa; this transmucosal delivery typically providing for delivery of substance into the crypts of lymphoid structures.

In this embodiment the second outlet unit 516 includes at least one outlet 528, in this embodiment a single nozzle, for delivering substance at the targeted mucosal surface.

In this embodiment the at least one outlet 528 is configured to provide a focused jet onto the targeted mucosal surface. In an alternative embodiment the at least one outlet 528 can be configured to provide a focused spray of particles which have a dimension and velocity such as to penetrate the mucosa; this transmucosal delivery typically providing for delivery of substance into the crypts of lymphoid structures.

In this embodiment the at least one outlet 528 is configured to target the adenoids directly, but in alternative embodiments delivery could be to other regions of the nasal cavity, where mucociliary transport delivers the substance to the adenoids. Such mucociliary transport also allows for delivery to the tonsils. In another alternative embodiment the at least one outlet 528 could be configured to deliver droplets to the floor of the nasal cavity, which substance would be transported to mucosal surfaces at the rear of the floor of the nasal cavity through mucociliary transport. Such delivery provides a regime which prevents the possibility of substance reaching the olfactory region, which is undesirable for some substances, particularly those containing neurotoxins.

The delivery unit 518 comprises a first substance supply unit 530 for delivering metered doses of substance to the first outlet unit 514, a second substance supply unit 532 for delivering metered doses of substance to the second outlet unit 516, and a breath-actuated trigger unit 538 for actuating the first and second substance supply units 530, 532 in response to exhalation by the user.

In this embodiment the first and second substance supply units 530, 532 comprise aerosol canisters for delivering metered doses of substance in a volume of propellant, preferably a hydrofluoroalkane (HFA) propellant or the like, which are fluidly connected to respective ones of the first and second outlet units 514, 516 to deliver substance from the at least one outlets 526, 528 thereof.

In this embodiment the first and second substance supply units 530, 532 are multi-dose units for delivering a plurality of metered doses of substance. In another embodiment the first and second substance supply units 530, 532 could be single-dose units for delivering single metered doses of substance.

The first and second substance supply units 530, 532 are pre-primeable, in this embodiment by loading a resilient element, and coupled to the trigger unit 538 such that, when the trigger unit 538 is actuated by the exhalation breath of the user, the resilient element is released to actuate the first and second substance supply units 530, 532 to deliver metered doses of substance through the at least one outlets 526, 528 of the respective ones of the first and second outlet units 514, 516.

In this embodiment the trigger unit 538 is configured to cause actuation of the first and second substance supply units 530, 532 on generation of a predetermined pressure thereat.

In an alternative embodiment the trigger unit 538 could be configured to cause actuation of the first and second substance supply units 530, 532 on generation of a predetermined flow rate therethrough.

In an alternative embodiment the first and second substance supply units 530, 532 could comprise mechanical delivery pumps, in particular liquid delivery pumps or powder delivery pumps, which deliver metered doses of substance on actuation thereof.

In another alternative embodiment the first and second substance supply units 530, 532 could comprise dry powder delivery units which deliver metered doses of substance on actuation thereof.

Operation of the delivery device will now be described hereinbelow.

Referring to FIG. 14(*a*), the first outlet unit 514 is first inserted into the oral cavity of the user above the tongue such that the mouthpiece 520 of the mouthpiece unit 510 is located at the teeth of the user, and the nosepiece 524 of the nosepiece unit 512 is fitted in one nostril such that the second outlet unit 516 is directed to the targeted mucosal surface, in this embodiment the adenoids.

The user then grips the mouthpiece 520 by biting thereon. Through this biting action, the teeth or the gums, in this embodiment the teeth, act to position the delivery device within the oral cavity, and in particular position the first outlet unit 514 within the oral cavity such that the at least one outlet 526 thereof is directed at the targeted mucosal surface, in this embodiment the palatine tonsil.

Referring to FIG. 14(*b*), the user then exhales through the mouthpiece 520, which exhalation causes the generation of a positive pressure in the oral cavity. This positive pressure acts both to close the oropharyngeal velum of the user and depress the tongue which facilitates access to the rear of the oral cavity, in particular the mucosal surfaces of the lymphoid structures to the rear of the oral cavity.

In this embodiment, when the pressure developed at the mouthpiece 520 reaches a predetermined value, the trigger unit 538 is triggered to actuate the first substance supply unit 530 to deliver a metered dose of substance to the at least one outlet 526 of the first outlet unit 514, with the at least one outlet 526 delivering a focused spray onto the targeted mucosal surface, and the second substance supply unit 532 to deliver a metered dose of substance to the at least one outlet 528 of the second outlet unit 516, with the at least one outlet 528 delivering a jet of substance onto the targeted mucosal surface.

In one embodiment, where the delivery device is a single-dose device, the device can be discarded.

In another embodiment, where the delivery device is a multi-dose device, the device is ready for further use following priming of the delivery unit 518.

In one alternative embodiment the delivery device could provide for delivery of substance to both of the nasal cavities. In this embodiment a nosepiece unit 512 would be provided to each of the nostrils.

FIGS. 15(*a*) and (*b*) illustrate an exhalation breath-actuated delivery device in accordance with a fourteenth embodiment of the present invention.

The delivery device of this embodiment is very similar to the delivery device of the above-described thirteenth embodiment, and thus, in order to avoid unnecessary duplication of description, only the differences will be described in detail, with like reference signs designating like parts.

The delivery device of this embodiment differs from that of the thirteenth-described embodiment only in that the nosepiece 524 of the nosepiece unit 512 includes a flow channel 540 which is fluidly connected to the flow channel 522 in the mouthpiece 520 of the mouthpiece unit 510.

With this configuration, the air flow generated by the exhalation breath of the user is delivered into the nasal cavity, and, as in this embodiment, where the air flow is at such a pressure as to flow around the posterior margin of the nasal septum, flows around the posterior margin of the nasal septum and out of the other nostril, thereby achieving bi-directional delivery as disclosed in the applicant's earlier WO-A-00/51672, the content of which is hereby incorporated by reference.

In one alternative embodiment the delivery device could be configured such that the pressure of the air flow to the one nostril is not sufficient to achieve bi-directional delivery through the nasal airway, with the air flow merely assisting delivery of substance.

In another alternative embodiment the delivery device could be configured such that the flow channel 522 in the mouthpiece 520 of the mouthpiece unit 510 is vented to atmosphere, and in further comprising a gas supply unit for delivering a gas flow, separate to the exhalation breath of the user, to the flow channel 540 in the nosepiece 524 of the nosepiece unit 512.

FIG. 16(*a*) to (*c*) illustrate a delivery device in accordance with a fifteenth embodiment of the present invention.

The delivery device of this embodiment finds particular application with subjects who are unable to cooperate, such as infants or unconscious patients.

The delivery device comprises a mouthpiece unit 610 which is located in the mouth of a subject, an outlet unit 614 which extends into the oral cavity of the subject and through which substance is delivered to mucosal surfaces of the oral cavity and a reflex-inducing fluid is delivered to the oral cavity, and a delivery unit 615 which is actuatable to deliver a volume of a gas, such as air, in actuating the delivery device, as will be described in more detail hereinbelow.

In this embodiment the substance is a vaccine, but in alternative embodiments can be a medicament.

In this embodiment the mouthpiece unit 610 includes a sucking element 620, upon which the subject sucks when located in the oral cavity as a consequence of the reflex sucking action.

The sucking element 620, in this embodiment in the form of an inflatable, elongate bulb member in the manner of a dummy or soother for an infant, is fluidly connected to the delivery unit 615 and configured, when inflated and sucked by the subject, such as to adopt a position against the hard palate, as illustrated in FIG. 16(*b*), such as both to fix the position of the outlet unit 614 relative to the hard palate and depress the tongue, as will be described in more detail hereinbelow.

In this embodiment the outlet unit 614 includes a first substance supply channel 628 which contains a volume of substance S and includes at least one outlet 630, in this embodiment a single nozzle, for delivering substance at a targeted mucosal surface to the rear of the oral cavity, here of the palatine tonsils, and a second reflex fluid supply channel 634 which includes at least one outlet 636, here a single nozzle, for delivering a reflex-inducing fluid, in this embodiment a gas, such as air, to the oral cavity of the subject, and in particular a posterior region of the oral cavity of the subject, in this embodiment the larynx, with the first and second channels 628, 634 being both fluidly connected to the delivery unit 615. The extent of the outlet unit 614 is configured to position the at least one outlet 630 of the first channel 628 thereof as far as possible to the rear of the oral cavity without causing discomfort or inducing the vomiting reflexes.

In this embodiment the at least one outlet 630 of the first channel 628 is configured to provide a focused spray onto the targeted mucosal surface. In an alternative embodiment the at least one outlet 630 of the first channel 628 can be configured to provide a focused spray of particles which have a dimension and velocity such as to penetrate the mucosa; this transmucosal delivery providing for the delivery of substance into the crypts of the lymphoid structure beneath the mucosa.

In this embodiment the substance S is contained within the first channel 628 by a pair of rupturable membranes 637, 638 which normally enclose the substance S and are ruptured by the pressure of the contained gas as developed by actuation of the delivery unit 615.

In an alternative embodiment the first channel 628 can be sized, typically in the form of a capillary channel, such that the substance S is ordinarily, absent an external influence, contained by the effect of surface tension.

As already described hereinabove, the delivery of a fluid, typically a gas or water, to the face of a subject, particularly an infant, is such as to cause a reflex action, often referred to as the diving reflex, which causes the vocal chords to close off the larynx and elevation of the oropharyngeal velum. By co-ordinating this reflex action and the delivery of substance such that the reflex action is elicited at the onset of delivery, the inhalation of substance can be prevented and the transfer of substance to the nasal cavity can be at least substantially prevented. In providing for this reflex action, improved delivery to non-compliant subjects, who may not otherwise provide velum closure, can be achieved. Such subjects are typically infants, and also animal subjects. It is envisaged that the delivery device could also possibly be utilized with unconscious subjects, non-cooperating human subjects, typically epileptics or comatosed patients.

In this embodiment the delivery unit 615 comprises a manually-actuatable balloon member 641 which, on compression, acts to inflate the sucker element 620 from a first, insertion configuration, as illustrated in FIG. 16(*a*), to a second, positioning configuration, as illustrated in FIG. 16(*b*), drive one gas flow, as a substance delivery flow, through the first, substance supply channel 128 which entrains the contained substance S and delivers the same from the at least one outlet 130 thereof to the targeted mucosal surface, and drive another gas flow, as a reflex-inducing gas flow, through the second, reflex fluid delivery channel 128 which is delivered from the at least one outlet 136 thereof as a reflex-inducing gas flow. In this embodiment the balloon member 641 is resiliently-biased such as to expand on release of the compressive, actuating force, which expansion of the balloon member 641 withdraws the volume of the contained gas from the sucker element 620 and contracts the same to the insertion configuration.

In an alternative embodiment the delivery unit 615 could comprise any gas supply unit, and, for example, in one embodiment could comprise a syringe.

In this embodiment the substance S can be a liquid or powder.

Operation of the delivery device will now be described hereinbelow.

Referring to FIG. 16(*a*), the sucker element 620 of the mouthpiece unit 610 is first inserted into the oral cavity of the subject above the tongue such that the sucker element 620 is located between the tongue and the hard palate.

The subject then, as a result of the reflex sucking action, sucks on the sucker element 620 of the mouthpiece unit 610.

With the mouthpiece unit 610 so inserted, the delivery unit 615 is then actuated, in this embodiment by compression of the balloon member 641.

In a first phase of the compression of the balloon member 641, as illustrated in FIG. 16(*b*), the sucker element 620 is inflated to the positioning configuration, and a gas flow, as a reflex-inducing gas flow, is delivered through the second channel 634.

Through this sucking action and the configuration of the sucker element 620 in the inflated, positioning configuration, the position of the mouthpiece unit 610 is fixed in the oral cavity, such as both to reference the direction of the outlet unit 614 by the sucker element 620 of the mouthpiece unit 610 acting on the hard palate, and cause the depression of the tongue which facilitates access to the rear of the oral cavity, in particular the mucosal surfaces of the lymphoid structures to the rear of the oral cavity.

And, through the gas flow to a posterior region of the oral cavity of the subject, the diving reflex is triggered, which causes the vocal chords to close off the larynx and elevation of the oropharyngeal velum.

In a second phase of the compression of the balloon member 641, as illustrated in FIG. 16(*c*), which follows as one continuous action from the first phase, the pressure of the gas contained in the balloon member 641 reaches the rupturing pressure of the substance-containing membranes 637, 638 such as to rupture the same, and a gas flow, as a substance supplying gas flow, is driven through the first channel 628 which entrains the substance S and delivers the same as a focused spray from the at least one outlet 130 thereof to the targeted mucosal surface.

In one alternative embodiment the sucker element 620 could be a solid, non-inflatable body.

In another alternative embodiment the delivery unit 615 could contain the substance S and comprise a three-compartment pump unit, typically a syringe, where a first compartment contains a metered amount of the substance S for delivery through the first, substance supply channel 628, a second compartment contains a gas which is delivered as a reflex-inducing gas flow through the second, reflex fluid supply channel 634, and a third compartment which contains a volume of gas which is delivered to the sucker element 620 such as to inflate the same. By phasing the delivery of the substance S and the gas flows from the respective compartments, the sucker element 620 can be fully inflated to the positioning configuration prior to the delivery of the substance S or the reflex-inducing gas flow, and the reflex-inducing gas flow can be initiated just prior to the delivery of the substance S.

Finally, it will be understood that the present invention has been described in its preferred embodiments and can be modified in many different ways without departing from the scope of the invention as defined by the appended claims.

In considering the described embodiments, it is important to recognize that features described in relation to any one of the described embodiments can be applied to any others of the described embodiments as modifications thereof.

For example, in the first-described embodiment the mouthpiece unit 10 could be configured such as to be a closed unit, thereby preventing the development of an exhalation air flow, and instead include a trigger element, such as a flexible diaphragm, which is moved to actuate the trigger unit 18 on generation of a predetermined actuation pressure in the oral cavity which is such as to cause closure of the oropharyngeal velum and depress the tongue to a position required for the at least one outlet 30 of the outlet unit 14 to be directed at the targeted mucosal surface. In an alternative embodiment, where the trigger unit 18 is electrically operated, the trigger unit 18 could be a pressure sensor.

In another example, the delivery device of the first-described embodiment could be manually actuated, where a user manually actuates the substance supply unit 16 subsequent to developing a sufficient pressure in the oral cavity. In one such embodiment the trigger unit 18 could be omitted entirely. In another such embodiment the trigger unit 18 could be modified to permit manual actuation on the development of a predetermined pressure at the mouthpiece 20 of the mouthpiece unit 10 and prevent manual actuation otherwise.

In another possible modification, in ones of the described embodiments the mouthpiece unit 10, 310, 410, 510 can be configured such that, following the establishment of a predetermined positive pressure in the oral cavity to close the oropharyngeal velum, the biting action provides the motive force for the delivery of substance, or is such as to release the motive force, for example, in breaking a mechanical link which is retaining the motive force.

Also, the delivery devices of most of the described preferred embodiments embody the substance as a liquid, but it will be understood that the delivery devices have equal application in relation to powders.

I claim:

1. A delivery device for delivering a substance into an oral cavity of a subject, the device comprising:
    a mouthpiece unit configured such that exhalation or attempted exhalation by the subject into the mouthpiece unit closes the oropharyngeal velum of the subject;
    an oral outlet unit including at least one substance outlet from which the substance is delivered into the oral cavity of the subject; and
    a substance supply unit which is actuatable to deliver the substance from the at least one substance outlet.

2. The delivery device of claim 1, further comprising a reflex-inducing fluid delivery unit for delivering a reflex-inducing fluid to the subject.

3. The delivery device of claim 2, further comprising a trigger unit configured to actuate both the substance supply unit and the reflex-inducing fluid delivery unit.

4. The delivery device of claim 1, further comprising a sucker element configured to fix the position of the at least one substance outlet relative to a hard palate of the subject.

5. The delivery device of claim 2, wherein the reflex-inducing fluid is air.

6. The delivery device of claim 2, wherein the reflex-inducing fluid is water.

7. The delivery device of claim 1, wherein the substance is a medicament.

8. The delivery device of claim 1, wherein the substance is a vaccine.

9. The delivery device of claim 1, wherein the oral outlet unit is targeted to deliver the substance to the palatine tonsils of the subject.

10. The delivery device of claim 1, wherein the oral outlet unit is targeted to deliver the substance to a mucosal surface within the oral cavity of the subject.

11. The delivery device of claim 1, wherein the substance supply unit delivers a metered dose of the substance.

12. A delivery device for delivering a substance into the oral cavity of a subject, the device comprising:
    a mouthpiece unit configured to be gripped in a mouth of the subject such that exhalation or attempted exhalation by the subject into the mouthpiece unit closes the oropharyngeal velum of the subject;
    an oral outlet unit including at least one substance outlet from which the substance is delivered into the oral cavity of the subject;
    an oral outlet unit positioner comprising a tongue depressor for depressing the tongue of the subject when the mouthpiece unit is gripped in the mouth of the subject.

13. The delivery device of claim 12, wherein the substance is a medicament.

14. The delivery device of claim 12, wherein the substance is a vaccine.

15. The delivery device of claim 12, wherein the tongue depressor is movable relative to the mouthpiece unit.

16. The delivery device of claim 12, wherein the oral outlet unit is targeted to deliver the substance to the palatine tonsils of the subject.

17. The delivery device of claim 12, wherein the mouthpiece unit comprises a mouthpiece including a flow channel through which the subject exhales to develop an exhalation air flow through the delivery device.

18. The delivery device of claim 12, further comprising a delivery unit comprising a substance supply unit which is actuatable to deliver the substance from the at least one substance outlet.

19. The delivery device of claim 18, further comprising a trigger unit configured to actuate the substance supply unit.

20. The delivery device of claim 18, wherein the substance supply unit contains multiple doses of the substance.

21. The delivery device of claim 18, wherein the substance supply unit delivers a metered dose of the substance.

22. The delivery unit of claim 12, wherein the substance is a powder.

* * * * *